United States Patent
Yount

(10) Patent No.: US 10,280,466 B2
(45) Date of Patent: *May 7, 2019

(54) METHOD AND KIT FOR DYNAMIC GENE EXPRESSION MONITORING

(71) Applicant: SUTTER BAY HOSPITALS, Emeryville, CA (US)

(72) Inventor: Garret L. Yount, San Francisco, CA (US)

(73) Assignee: Institute of Noetic Sciences, Petaluma, CA (US)

( * ) Notice: Subject to any disclaimer, the term of this patent is extended or adjusted under 35 U.S.C. 154(b) by 336 days.

This patent is subject to a terminal disclaimer.

(21) Appl. No.: 15/173,993

(22) Filed: Jun. 6, 2016

(65) Prior Publication Data

US 2017/0002415 A1  Jan. 5, 2017

Related U.S. Application Data

(63) Continuation of application No. 12/601,592, filed as application No. PCT/US2008/066407 on Jun. 10, 2008, now Pat. No. 9,360,489.

(60) Provisional application No. 60/943,095, filed on Jun. 11, 2007, provisional application No. 60/970,221, filed on Sep. 5, 2007.

(51) Int. Cl.

| | | |
|---|---|---|
| *G01N 33/48* | (2006.01) | |
| *G01N 33/50* | (2006.01) | |
| *C12Q 1/6883* | (2018.01) | |
| *G06F 19/12* | (2011.01) | |
| *G06F 19/24* | (2011.01) | |
| *G06F 19/20* | (2011.01) | |
| *G01N 33/68* | (2006.01) | |
| *G06F 19/18* | (2011.01) | |

(52) U.S. Cl.
CPC ....... *C12Q 1/6883* (2013.01); *G01N 33/6896* (2013.01); *G06F 19/12* (2013.01); *G06F 19/20* (2013.01); *G06F 19/24* (2013.01); *C12Q 2600/106* (2013.01); *C12Q 2600/158* (2013.01); *G01N 2800/30* (2013.01); *G06F 19/18* (2013.01)

(58) Field of Classification Search
None
See application file for complete search history.

(56) References Cited

U.S. PATENT DOCUMENTS

| | | |
|---|---|---|
| 3,545,435 A | 12/1970 | Augenstein et al. |
| 5,576,177 A | 11/1996 | Fridland et al. |
| 5,604,103 A | 2/1997 | Thomas et al. |
| 6,133,419 A * | 10/2000 | Braselmann ........... C07K 14/47 435/320.1 |
| 6,561,970 B1 | 5/2003 | Carpenter et al. |
| 6,911,435 B1 * | 6/2005 | Cohn ............... A61K 31/70 514/46 |
| 9,360,489 B2 * | 6/2016 | Yount ............ G01N 33/6896 |
| 2002/0077581 A1 | 6/2002 | Davidner et al. |
| 2002/0197604 A1 | 12/2002 | Rheins et al. |
| 2004/0033613 A1 | 2/2004 | Zwick et al. |
| 2005/0208519 A1 | 9/2005 | Liew et al. |
| 2005/0287576 A1 | 12/2005 | Bevilacqua et al. |
| 2006/0121485 A1 | 6/2006 | Coy |
| 2007/0031832 A1 | 2/2007 | Watt et al. |
| 2007/0099203 A1 | 5/2007 | Zhang |

FOREIGN PATENT DOCUMENTS

| | | |
|---|---|---|
| WO | 2004030511 A2 | 4/2004 |
| WO | 2007062995 A2 | 6/2007 |
| WO | 2008154532 A1 | 12/2008 |

OTHER PUBLICATIONS

Akpek et al., "Use of oral mucosal neutrophil counts to detect the onset and resolution of profound neutropenia following high dose myelosuppressive chemotherapy," Am. J. of Hematol., 72:13-19, 2003.

Lactoferring, Mosby's Dental Dictonary 2008, http://credoreference.com/entry/ehsdent/lcatoferrin.

Moyse, Ellen, International Preliminary Report on Patentability and Written Opinion, dated Dec. 11, 2009; International Application No. PCT/US2008/066407.

* cited by examiner

*Primary Examiner* — Russell S Negin

(74) *Attorney, Agent, or Firm* — Gavrilovich, Dodd & Lindsey LLP

(57) ABSTRACT

This disclosure relates to methods and kits, systems for screening, diagnosing and prognosing a disease, disorder, or physiological state based upon temporal measurements and analysis of gene expression in a subject.

17 Claims, 3 Drawing Sheets

METHOD AND KIT FOR DYNAMIC GENE EXPRESSION MONITORING

CROSS REFERENCE TO RELATED APPLICATIONS

The application is a continuation of U.S. application Ser. No. 12/601,592, filed Nov. 24, 2009, which is a U.S. National Stage Application filed under 35 U.S.C. § 371 and claims priority to International Application No. PCT/US08/066407, filed Jun. 10, 2008, which application claims priority under 35 U.S.C. § 119 to U.S. Provisional Application Ser. Nos. 60/943,095, filed Jun. 11, 2007 and 60/970,221, filed Sep. 5, 2007, the disclosures of which are incorporated herein by reference.

FIELD OF THE INVENTION

This invention relates to methods and kits, systems for screening, diagnosing and prognosing a disease, disorder, or physiological state based upon temporal measurements and analysis of gene expression in a subject.

BACKGROUND

Cells and tissues are influenced by endogenous and exogenous agents and respond with a cascade of biological activities to mediate a response to an agent. Gene expression provides phenotypic changes in a subject often associated with disease, disorder, or physiological state occurrence and progression.

SUMMARY

The disclosure provides a method of monitoring a subject's mental, emotional or physical state. The method includes obtaining a first biological sample from the subject at a first time point; quantifying the amounts of a set of biological factors in the first biological sample; obtaining a second biological sample from the subject at a second time point; quantifying the amounts of a set of biological factors in the second biological sample; and determining a change in the quantified biological factors between the first sample and the second sample, wherein the change in the biological factors between the first sample and the second sample is indicative of the subject's mental, emotional or physical state.

The disclosure also provides a method of monitoring a subject's mental, emotional or physical state. The method includes obtaining a first salivary sample from the subject at a first time point; fixing a set of biological factors in the first salivary sample; obtaining a second salivary sample from the subject at a second time point; fixing a set of biological factors in the second salivary sample; quantifying biological factors in the first and the second salivary samples; and determining a change in the quantified biological factors between the first sample and the second sample, wherein the change in the biological factors between the first sample and the second sample is indicative of the subject's mental, emotional or physical state.

The disclosure also provides a system for monitoring a subject's mental, emotional or physical state. The method includes obtaining a first biological sample from the subject at a first time point; quantifying the amounts of a set of polynucleotides or polypeptides in the first biological sample; obtaining a second biological sample from the subject at a second time point; quantifying the amounts of a set of polynucleotides or polypeptides in the second biological sample; and determining a change in the quantified polynucleotides or polypeptides between the first sample and the second sample, wherein the change in the polynucleotides or polypeptides between the first sample and the second sample is indicative of the subject's mental, emotional or physical state and wherein the quantifying and determining a change are performed using a computer.

The disclosure provides a method of monitoring a subject's mental, emotional or physical state. The method includes obtaining a first biological sample from the subject at a first time point; quantifying the amounts of a set of biological factors in the first biological sample; obtaining a second biological sample from the subject at a second time point; quantifying the amounts of a set of biological factors in the second biological sample; and determining a change in the quantified biological factors between the first sample and the second sample, wherein the change in the biological factors between the first sample and the second sample is indicative of the subject's mental, emotional or physical state.

The disclosure also provides a method of monitoring a subject's mental, emotional or physical state, comprising obtaining a first salivary sample from the subject at a first time point; fixing a set of biological factors in the first salivary sample; obtaining a second salivary sample from the subject at a second time point; fixing a set of biological factors in the second salivary sample; quantifying biological factors in the first and the second salivary samples; and determining a change in the quantified biological factors between the first sample and the second sample, wherein the change in the biological factors between the first sample and the second sample is indicative of the subject's mental, emotional or physical state.

Also provided are kits useful for carrying out the methods of the disclosure. For example, the kit can be compartmentalized to contain reagents for collection of biological factors such as Hanks Balanced Salt Solution and a fixing agent such as formaldehyde or alcohol. In addition, the kit may contain detection system or vessel used to transmit information to a remote location. The kit may comprise a device for detection of a biological factor in the sample that is collected (e.g., a microarray, an ELISA system and the like).

The disclosure also provides a system for monitoring a subject's mental, emotional or physical state, comprising: a computer; a computer program on the computer comprising instructions to: quantify the amounts of a set of biological factors in a first biological sample; store the quantified amounts from the first biological sample in a computer; quantify the amounts of a set of biological factors in a second biological sample; and determine a change in the quantified polynucleotides or polypeptides between the first sample and the second sample using the first stored quantified amounts and the second quantified amount, wherein the change in the polynucleotides or polypeptides between the first sample and the second sample is indicative of the subject's mental, emotional or physical state; and output the measured change, the mental, emotion or physical state associated with the measured change or a combination thereof to a technician or user.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
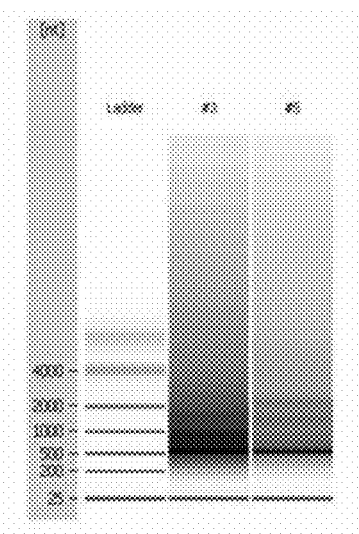
FIG. 1A shows a Gel image of amplified cDNAs. Oral neutrophils fixed with formaldehyde or paraformaldehyde and used as source of mRNA. Global PCR amplification of mRNA yielded cDNA of sufficiently high quality for gene expression analysis as determined by gel electrophoresis.

As used herein and in the appended claims, the singular forms "a," "and," and "the" include plural referents unless the context clearly dictates otherwise. Thus, for example, reference to "a polynucleotide" includes a plurality of such polynucleotides and reference to "the marker" includes reference to one or more markers known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Gene expression can be examined by analyzing nucleic acids (e.g.: DNA, RNA) extracted from cells of a subject. To capture sufficient genetic materials, the cells must remain intact. When cells are removed from the body, the structure of individual cells should be stabilized by cytological processing. mRNA is unstable and easily degraded by RNases and to do a meaningful analysis, mRNA must be preserved. In other words, a valuable analysis is possible only if mRNA degradation is prevented. Many preservative compositions and fixatives cause irreversible damage to the structure of nucleic acids (e.g., DNA, and especially RNA) and reduce their yield, thereby limiting the usefulness of genetic analysis for clinical and research purposes. Suitable compositions for the preservation and/or storage of a cell should be used so that autolysis is prevented and that cellular morphology and mRNA are maintained until processing.

Signals regulating gene expression can be generated as a result of human activities and experiences ranging from physical exercise to psychological stress. The fact that the expression level of genes goes up or down according to a person's stress level indicates that mental activity can influence the way our genetic "operating instructions" are carried out. This indication stems from the fact that humans are able to use psychological tools such, as meditation and visualization, to alter stress levels. For example, gene regulation is involved in mental states as subtle as expectation of pain or placebo effects; when subjects in the placebo study believed they were receiving a pain reliever, their brains released more endogenous opioids which act as natural painkillers by blocking transmission of pain signals between neurons. The activation of pain-suppressive, endogenous opioid neurotransmission involves the up-regulation of opioid genes to produce the opioid peptides for release. Since opioid genes are regulated by early response genes that must be up-regulated first, these data demonstrate indirectly that purely mental processes involved in expectation can trigger up-regulation of early response gene and opioid gene expression (See FIG. 1B).

Monitoring dynamic genetic changes through screening genetic materials of cells can be achieved only if cellular degradation is prevented. Convenient methods to collect suitable samples while preserving cellular integrity is essential to achieving an efficient genetic analysis.

The disclosure provides a method, system and kits for monitoring of biological changes in a subject. In another aspect, the disclosure provides methods of determining the risk of, diagnosis of, or prognosis of a disease or disorder, or physiological state. The methods, systems and kits of the disclosure are useful for obtaining and preserving biological samples, for use in monitoring gene expression changes in a subject.

In some aspects of the disclosure, the monitoring of gene expression changes is obtained at a home, and may be remotely determined. The biological sample is acquired at a plurality of time points. A change in the expression of a marker or plurality of markers measured temporally can provide data indicative of various phenotypic changes, diseases or disorders. These biological factors can then be characterized to indicate the presence of a local or systemic response in the subject.

Figure 2:
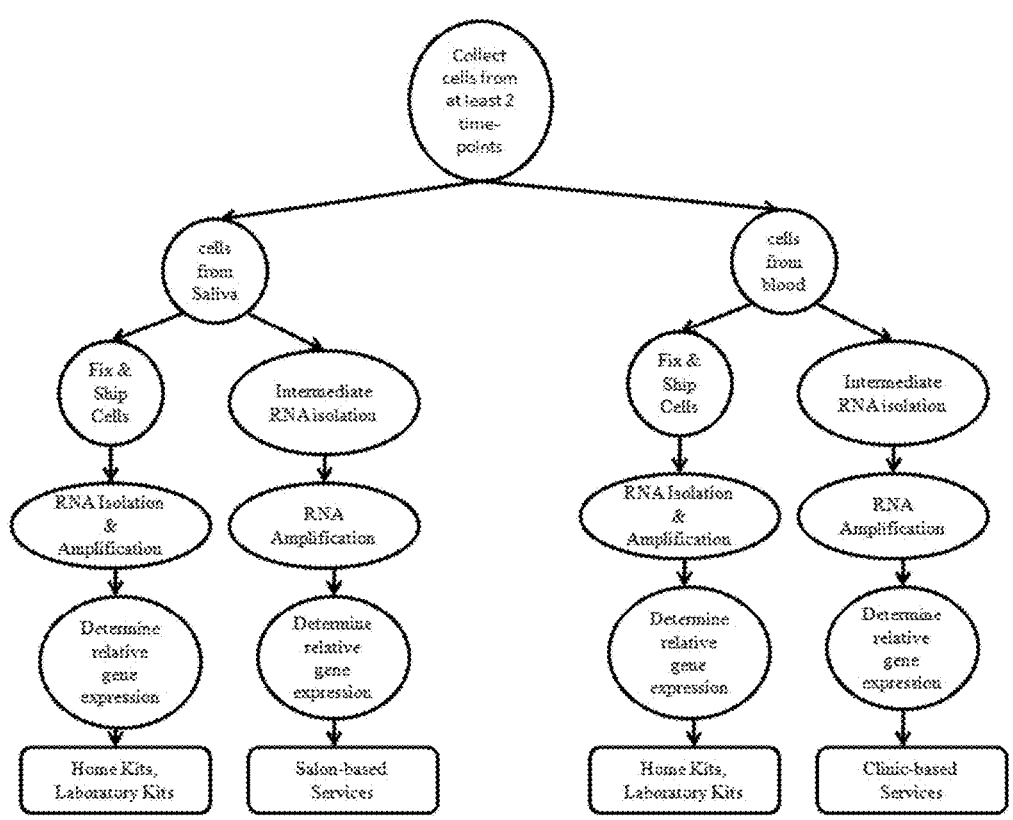
FIG. 2 shows exemplary processing pathways of the disclosure.

The process begins with the collection of samples at two or more times and results in the subject receiving personal information related to the dynamic state of their genes (FIG. 2). There are numerous methods of obtaining biological samples comprising a biological factor (e.g., a polynucleotide) useful for obtaining gene expression profiles.

In one embodiment, the sample is collected from the mouth of a subject. For example, the mouth comprises a number of different cell types including epithelial, mucosal, eosinophils, macrophages, neutrophils and the like. Samples from the mouth of a subject can be obtained non-invasively by swab, saliva or a wash. It will be recognized the certain biological molecules are easily degraded due to enzymes also found in these same cells or samples (RNAses). Once a sample is obtained fixing the sample to prevent degradation and to obtain proper sample representation should be performed. In one aspect, the sample is obtain by washing the e.g., mouth with a balanced salt solution (e.g., HBSS) and collecting the wash in a sample reservoir. In a further aspect, the sample reservoir can comprise a fixative such as formaldehyde to prevent degradation. In another aspect, a fixative is mixed with the sample after collection. Other methods will be apparent for collection of samples for performance of the methods described herein.

For example, in some instances the sample will be obtained from a location of a subject related to the disease, disorder, or physiological state to be detected. Samples may be isolated by any number of means well known in the art. For example, non-invasive methods for collecting a biological factor, such as polynucleotides, from skin cells below the stratum corneum can be used to measure changes of skin cells (e.g., related to inflammation or dermatitis). In another aspect, a non-invasive method includes the collection of saliva, urine or fecal matter. In yet another aspect, a minimally invasive method includes the collection by swabbing the buccal or rectal region of a subject. Invasive methods of collection of a biological sample include the collection of blood, serum or scrapings of a tissue. The blood or serum can be collected by pricking the skin or by collection of a larger volume of blood through aspiration of blood from a vein. Thus, a biological sample for use in the methods of the disclosure can comprise any of the following: serum, blood, saliva, sputum, urine, fecal matter, tissue samples, and the like, so long as a polynucleotide or polypeptide marker is present in the biological sample. These biological factors can then be characterized to indicate the presence of a local or systemic response in the subject.

As a result of scientific advances in the field of genomics, the search for biomarkers associated with health or diseases and disorders has been intensified. Non-invasive means for collecting and monitoring biomarkers are highly desirable as they lead not only to subject convenience and increased compliance, but also to a safe and efficient point-of-care mechanism suitable in remote or impoverished settings. The use of biofluid saliva to monitor health and disease state of an individual is gaining popularity. Saliva is the mirror of the body and it contains biological factors indicative of an individual's health or disease state (Li et al, 2005). Accordingly, in one embodiment, the sample will be obtained from saliva. The subject will rinse mouth with an oral rinse and then eject saliva into a collection device. An oral rinse assay could include an osmotically balanced solution (e.g.: normal saline, Hank's Balanced Salt Solution).

Biological factors in saliva can be extracted and analyzed by any number of means well known in the art. Extraction of saliva content such as RNA extraction from cell-free saliva has been used to perform genetic analysis (Wong Ser. No. 11/531,967-A1-20070117123).

Although extracellular RNA and proteins have been used to detect diseases (Li et al, 2005), a preferred embodiment of the disclosure describes collection of cellular components in saliva such as neutrophils. Neutrophils are plentiful in saliva. There is a continuous influx of neutrophils into the saliva as the immune system acts to eradicate infective agents in the mouth (Bender et al. 2006). Neutrophils can be collected by rinsing the mouth with an osmotically balanced solution (e.g.: normal saline, Hank's Balanced Salt Solution). Samples may be isolated by any number of means well known in the art. Invasive methods for isolating a sample include the use of needles, for example during blood sampling, as well as biopsies of various tissues. The disclosure provides a method and kit useful for non-invasively, minimally invasive or invasively obtaining a sample which may be used as a source for obtaining biological factors in the detection, diagnosis, or prognosis of various diseases, disorders, or inflammatory reactions.

Figure 3:
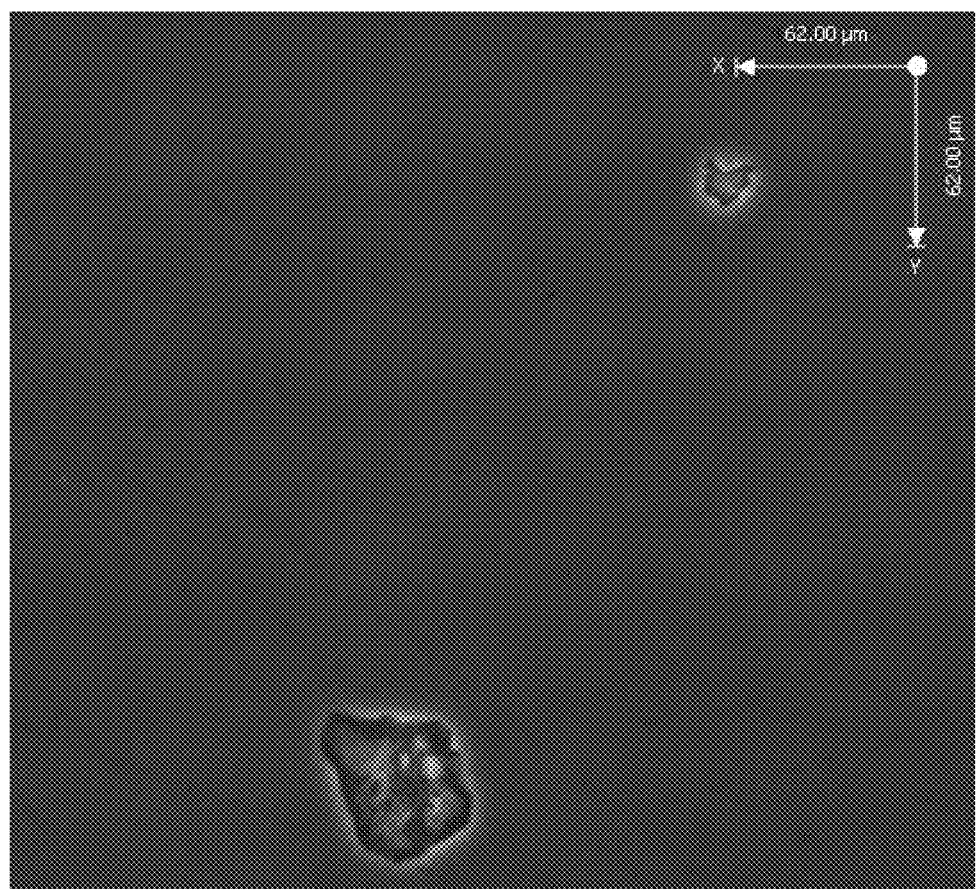
FIG. 3 shows neutrophils are easily isolated from epithelial Cells by size. Neutrophils are between about 9 and 16 microns in size and can be isolated by filtration.

Neutrophils are easily collected from saliva samples (Ashkenazi and Dennison 1989), (Bender, Thang et al. 2006) and separated from oral epithelial cells and debris by size (See FIG. 3). Neutrophils are capable of extensive, rapid, and complex changes in gene expression (Newburger, Subrahmanyam et al. 2000), (Roy, Khanna et al. 2005).

Preservation of nucleic acids in a fresh cell usually requires special handling, such as immediate processing or freezing, to allow examination by a combination of cytologic and genetic techniques. A valuable mRNA analysis is possible only if mRNA degradation is prevented and macromolecular structures are stabilized.

Any number of preservation techniques known in the art can be used. Suitable compositions for the preservation and/or storage of a cell would ensure that autolysis is prevented and that cellular morphology and mRNA are maintained until processing. Any number of means well known in the art can be used to preserve the Sample. Many preservative compositions and fixatives cause irreversible damage to the structure of nucleic acids (e.g., DNA, and especially RNA) and reduce their yield, thereby limiting the usefulness of genetic analysis.

Any number of fixative agents that are known in the art can be used. The usual formulations for fixing of cells contain one or more agents which react with the cells. Typical of this type of agent is formaldehyde or paraformaldehyde, picric acid, mercuric ions and glutaraldehyde. In addition, alcohol may be used as a fixative agent.

In one embodiment, the saliva sample is fixed using a fixative agent such as formaldehyde or paraformaldehyde. The fixative agent disables intrinsic biomolecules (e.g.: RNAses) so that samples can be stored for RNA isolation at a later time. In an embodiment of the disclosure, formaldehyde solution at a concentration of 37% W/W is added to the saliva sample at a final concentration of 2.3% and samples are stored at 4 degree centigrade.

As used herein, the term "fixative agent" refers to an agent suitable for the preservation and stabilization of a cell that would ensure autolysis is prevented and that cellular morphology and mRNA are maintained until a later time. An example of a fixative agent includes formaldehyde or paraformaldehyde, picric acid, mercuric ions, glutaraldehyde, and alcohol.

"Fixing" as used herein refers to a process of preservation and stabilization preventing autolysis, destruction, and damage to cells or the biological factors contained therein. For example, fixing cellular components with a fixative agent can result in preservation of cells containing one or more agents.

A limitation on use of RNA expression analysis has been the requirement for high-quality RNA derived from samples. Some reports have concluded that RT-PCR-based methods from formalin-fixed paraffin-embedded (FFPE) for genome-wide microarray analysis do not perform well because only a minority of FFPE blocks could be analyzed (Penland, Keku et al. 2007), (Amary, Berisha et al. 2007). While other reports have shown gene expression profiling using formalin-fixed, paraffin-embedded (FFPE) cancer cells was efficient.

In one embodiment of this disclosure, the saliva sample is fixed using a fixative agent such as formaldehyde or paraformaldehyde.

Other reports show that RNA retrieved from formalin-fixed, paraffin-embedded (FFPE) tissues result in fragmented RNA and a lower yield. These reports demonstrate that for immersion fixation of brains, 70% ethanol is superior to formalin for mRNA preservation. (Su, Perlaky et al. 2004).

Similar reports demonstrate that consistent results are more easily obtainable using ethanol-fixed tissues, whereas formalin-fixed tissue does not typically provide a useful substrate for cDNA synthesis and labeling (Karsten, Van Deerlin et al. 2002).

In another embodiment of this disclosure, the saliva sample is fixed using a fixative agent such as alcohol.

In one embodiment, neutrophils are separated from epithelial cells and other debris in the saliva by filtration. These oral neutrophils fixed with formaldehyde or paraformaldehyde is then used as source of mRNA for gene expression analysis.

Various types of amplification techniques are now well-developed to enable gene expression analysis from a small number of cells (Ginsberg 2005), (Ozawa, Kishi et al. 2006), (Paludan and Thestrup-Pedersen 1992), (Kim, Dix et al. 2006), (Laurell, Wirta et al. 2007), (Kurimoto, Yabuta et al. 2007), (Kube, Savci-Heijink et al. 2007). The specific protocols employed will depend upon practical aspects that will likely differ between applications.

A biological factor obtained from any in vitro or in vivo biological sample, in purified or non-purified form, can be used as the starting material. As used herein, the term "biological factor" means any number of factors that have biological activity or play a biological role. For example, biological factor includes polynucleotides, such as DNA, RNA, mRNA and cDNA, polypeptides, including those identified in Table 1 (attached hereto) fragments thereof, as well as lipids such as cholesterol, fatty acids, and inflammatory mediators such as leukotrienes, prostaglandins and others produced by enzymatic activity results from DNA transcription and polypeptide expression.

The disclosure provides a method for obtaining polynucleotides, such as mRNA, which are helpful to establish changes in the synthetic patterns of the subject's cells or organ systems. Various methods can be used to amplify and/or detect such polynucleotides as described more fully herein.

As used herein, the terms "nucleic acid," "polynucleotide," or "nucleic acid sequence" refer to a polymer of deoxyribonucleotides or ribonucleotides, in the form of a separate fragment or as a component of a larger construct. Polynucleotide or nucleic acid sequences of the disclosure include DNA, RNA, including mRNA and cDNA sequences.

Polynucleotides can be obtained from the biological sample using any number of techniques known in the art. Where the sample comprises cells, the cells may be first lysed, followed by purification and/or amplification of the polynucleotide.

As used herein, the term "polypeptide" refers to a polymer of amino acid residues in the form of a separate fragment or component of a larger construct. An example of a polypeptide includes amino acid sequences encoding a cytokine or fragments thereof. A polypeptide may encode for a functional protein or fragments of a protein. For example, an IL-4 polypeptide includes the full length protein sequence of IL-4 as well as fragments thereof consisting of a polymer of amino acids.

"Cytokine" as used herein means any number of factors that play a role in cellular regulation or differentiation. For example, cytokines can include the family of interleukins (IL) including IL-1, IL-2, IL-3, IL-4, IL-5, IL-6, IL-8, IL-9, IL-13, IL-14 as well as factors belonging to the transforming growth factor beta (TGF-β) superfamily, GM-CSF and interferon.

Polynucleotides can be isolated from the lysed cells and cellular material by any number of means well known to those skilled in the art. For example, a number of commercial products are available for isolating polynucleotides, including but not limited to, TriReagent (Molecular Research Center, Inc, Cincinnati, Ohio) may be used. The isolated polynucleotides can then be tested or assayed for particular nucleic acid sequences, including a polynucleotide encoding a cytokine.

Consequently, the process may employ, for example, DNA or RNA, including messenger RNA (mRNA), isolated from a tissue. The DNA or RNA may be single stranded or double stranded. When RNA is obtained, enzymes and conditions optimal for reverse transcribing the template to DNA well known in the art can be used. Alternatively, the RNA can be subjected to RNAse protection assays. A DNA-RNA hybrid that contains one strand of each may also be used. A mixture of polynucleotides may also be employed, or the polynucleotides produced in a previous amplification reaction, using the same or different primers may be so used. In the instance where the polynucleotide sequence is to be amplified the polynucleotide sequence may be a fraction of a larger molecule or can be present initially as a discrete molecule, such that the specific sequence is the entire nucleic acid. It is not necessary that the sequence to be amplified be present initially in a pure form; it may be a minor fraction of a complex mixture, such as contained in whole human DNA.

A probe refers to a molecule which can detectably distinguish changes in gene expression or can distinguish between target molecules differing in structure. Detection can be accomplished in a variety of different ways depending on the type of probe used and the type of target molecule. Thus, for example, detection may be based on discrimination of activity levels of the target molecule, but typically is based on detection of specific binding. Examples of such specific binding include antibody binding and nucleic acid probe hybridization. Thus, for example, probes can include enzyme substrates, antibodies and antibody fragments, and nucleic acid hybridization probes (including primers useful for polynucleotide amplification and/or detection). Thus, in one embodiment, the detection of the presence or absence of the at least one target polynucleotide involves contacting a biological sample with a probe, typically an oligonucleotide probe, where the probe hybridizes with a form of a target polynucleotide in the biological sample containing a complementary sequence, where the hybridization is carried out under selective hybridization conditions. Such an oligonucleotide probe can include one or more nucleic acid analogs, labels or other substituents or moieties so long as the base-pairing function is retained.

An oligonucleotide probe or a primer refers to a nucleic acid molecule of between 8 and 2000 nucleotides in length, or is specified to be about 6 and 1000 nucleotides in length. More particularly, the length of these oligonucleotides can range from about 8, 10, 15, 20, or 30 to 100 nucleotides, but will typically be about 10 to 50 (e.g., 15 to 30 nucleotides). The appropriate length for oligonucleotides in assays of the disclosure under a particular set of conditions may be empirically determined by one of skill in the art.

Oligonucleotide primers and probes can be prepared by any suitable method, including, for example, cloning and restriction of appropriate sequences and direct chemical synthesis. One of skill will be capable of identifying appropriate probes and primer pairs from the polynucleotide sequence referenced in Table 1.

Oligonucleotide probes and primers can comprise nucleic acid analogs such as, for example peptide nucleic acids, locked nucleic acid (LNA) analogs, and morpholino analogs. The 3' end of the probe can be functionalized with a capture or detectable label to assist in detection of a target polynucleotide or of a polymorphism.

Any of the oligonucleotides or nucleic acids of the disclosure can be labeled by incorporating a detectable label measurable by spectroscopic, photochemical, biochemical, immunochemical, or chemical means. For example, such labels can comprise radioactive substances (32P, 35S, 3H, 125I), fluorescent dyes (5-bromodesoxyuridin, fluorescein, acetylaminofluorene, digoxigenin), biotin, nanoparticles, and the like. Such oligonucleotides are typically labeled at their 3' and 5' ends.

A reference or control population refers to a group of subjects or individuals who are predicted to be representative of the genetic variation found in the general population having a particular genotype or expression profile. Typically, the reference population represents the genetic variation in the population at a certainty level of at least 85%, typically at least 90%, least 95% and but commonly at least 99%.

A subject comprises an individual (e.g., a mammalian subject or human) whose gene expression profile, genotypes or haplotypes or response to treatment or disease state or change in physiological state are to be determined.

In addition, RNAse protection assays may be used if RNA is the polynucleotide obtained from the sample. In this procedure, a labeled antisense RNA probe is hybridized to the complementary polynucleotide in the sample. The remaining unhybridized single-stranded probe is degraded by ribonuclease treatment. The hybridized, double stranded probe is protected from RNAse digestion. After an appropriate time, the products of the digestion reaction are collected and analyzed on a gel (see for example Ausubel et al., CURRENT PROTOCOLS IN MOLECULAR BIOLOGY, section 4.7.1 (1987)). As used herein, "RNA probe" refers to a ribonucleotide capable of hybridizing to RNA in a sample of interest. Those skilled in the art will be able to identify and modify the RNAse protection assay specific to the polynucleotide to be measured, for example, probe specificity may be altered, hybridization temperatures, quantity of nucleic acid etc. Additionally, a number of commercial kits are available, for example, RiboQuant™ Multi-Probe RNAse Protection Assay System (Pharmingen, Inc., San Diego, Calif.).

In another embodiment, the polynucleotide in the sample may be analyzed by Northern or Southern blot. In this technique the polynucleotides are separated on a gel and then probed with a complementary polynucleotide to the sequence of interest. For example, RNA is separated on a gel transferred to nitrocellulose and probed with complementary DNA to the sequence of interest. The complementary probe may be labeled radioactively, chemically etc. Hybridization of the probe is indicative of the presence of the polynucleotide of interest.

Detection of a polynucleotide encoding a cytokine may be performed by standard methods such as size fractionating the nucleic acid. Methods of size fractionating the DNA and RNA are well known to those of skill in the art, such as by gel electrophoresis, including polyacrylamide gel electrophoresis (PAGE). For example, the gel may be a denaturing 7 M or 8 M urea-polyacrylamide-formamide gel, Size fractionating the nucleic acid may also be accomplished by chromatographic methods known to those of skill in the art.

The detection of polynucleotides may optionally be performed by using radioactively labeled probes. Any radioactive label may be employed which provides an adequate signal. Other labels include ligands, colored dyes, and fluorescent molecules, which can serve as a specific binding pair member for a labeled ligand, and the like. The labeled preparations are used to probe for a polynucleotide by the Southern or Northern hybridization techniques, for example. Nucleotides obtained from samples are transferred to filters that bind polynucleotides. After exposure to the labeled polynucleotide probe, which will hybridize to nucleotide fragments containing target nucleic acid sequences, the binding of the radioactive probe to target nucleic acid fragments is identified by autoradiography (see Genetic Engineering, 1 ed. Robert Williamson, Academic Press (1981), pp. 72-81). The particular hybridization technique is not essential to the disclosure. Hybridization techniques are well known or easily ascertained by one of ordinary skill in the art. As improvements are made in hybridization techniques, they can readily be applied in the method of the disclosure.

Any of the oligonucleotide primers and probes of the disclosure can be immobilized on a solid support. Solid supports are known to those skilled in the art and include the walls of wells of a reaction tray, test tubes, polystyrene beads, magnetic beads, nitrocellulose strips, membranes, and microparticles such as latex particles, glass, microfluidic devices and the like. The solid support is not critical and can be selected by one skilled in the art. Thus, latex particles, microparticles, magnetic or non-magnetic beads, membranes, plastic tubes, walls of microtiter wells, glass or silicon chips and the like are all suitable examples. Suitable methods for immobilizing oligonucleotides on a solid phase include ionic, hydrophobic, covalent interactions and the like. The solid support can be chosen for its intrinsic ability to attract and immobilize the capture reagent. The oligonucleotide probes or primers of the disclosure can be attached to or immobilized on a solid support individually or in groups of about 2-10,000 distinct oligonucleotides of the disclosure to a single solid support.

A substrate comprising a plurality of oligonucleotide primers or probes of the disclosure may be used either for detecting or amplifying targeted sequences.

The oligonucleotide probes and primers of the disclosure can be attached in contiguous regions or at random locations on the solid support. Alternatively the oligonucleotides of the disclosure may be attached in an ordered array wherein each oligonucleotide is attached to a distinct region of the solid support which does not overlap with the attachment site of any other oligonucleotide. Typically, such oligonucleotide arrays are "addressable" such that distinct locations are recorded and can be accessed as part of an assay procedure. The knowledge of the location of oligonucleotides on an array makes "addressable" arrays useful in hybridization assays. For example, the oligonucleotide probes can be used in an oligonucleotide chip such as those marketed by Affymetrix and described in U.S. Pat. No. 5,143,854; PCT publications WO 90/15070 and 92/10092, the disclosures of which are incorporated herein by reference. These arrays can be produced using mechanical synthesis methods or light directed synthesis methods which incorporate a combination of photolithographic methods and solid phase oligonucleotide synthesis.

The immobilization of arrays of oligonucleotides on solid supports has been rendered possible by the development of a technology generally referred to as "Very Large Scale Immobilized Polymer Synthesis" in which probes are immobilized in a high density array on a solid surface of a chip (see, e.g., U.S. Pat. Nos. 5,143,854; and 5,412,087 and in PCT Publications WO 90/15070, WO 92/10092 and WO 95/11995, each of which are incorporated herein by reference), which describe methods for forming oligonucleotide arrays through techniques such as light-directed synthesis techniques.

The polynucleotides encoding the desired polypeptide may be amplified before detecting. The term "amplified" refers to the process of making multiple copies of the nucleic acid from a single polynucleotide molecule. The amplification of polynucleotides can be carried out in vitro by biochemical processes known to those of skill in the art. The amplification agent may be any compound or system that will function to accomplish the synthesis of primer extension products, including enzymes. Suitable enzymes for this purpose include, for example, E. coli DNA polymerase I, Taq polymerase, Klenow fragment of E. coli DNA polymerase I, T4 DNA polymerase, other available DNA polymerases, polymerase muteins, reverse transcriptase, ligase, and other enzymes, including heat-stable enzymes (i.e., those enzymes that perform primer extension after being subjected to temperatures sufficiently elevated to cause denaturation). Suitable enzymes will facilitate combination of the nucleotides in the proper manner to form the primer extension products that are complementary to each mutant nucleotide strand. Generally, the synthesis will be initiated at the 3'-end of each primer and proceed in the 5'-direction along the template strand, until synthesis terminates, producing molecules of different lengths. There may be amplification agents, however, that initiate synthesis at the 5'-end and proceed in the other direction, using the same process as described above. In any event, the method of the disclosure is not to be limited to the embodiments of amplification described herein.

One method of in vitro amplification which can be used according to this disclosure is the polymerase chain reaction (PCR) described in U.S. Pat. Nos. 4,683,202 and 4,683,195. The term "polymerase chain reaction" refers to a method for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation and dissociation produce rapid and highly specific amplification of the desired sequence. The polymerase chain reaction is used to detect the presence of polynucleotides encoding cytokines in the sample. Many polymerase chain methods are known to those of skill in the art and may be used in the method of the disclosure. For example, DNA can be subjected to 30 to 35 cycles of amplification in a thermocycler as follows: 95° C. for 30 sec, 52° to 60° C. for 1 min, and 72° C. for 1 min, with a final extension step of 72° C. for 5 min. For another example, DNA can be subjected to 35 polymerase chain reaction cycles in a thermocycler at a denaturing temperature of 95° C. for 30 sec, followed by varying annealing temperatures ranging from 54-58° C. for 1 min, an extension step at 70° C. for 1 min and a final extension step at 70° C.

The primers for use in amplifying the polynucleotides of the disclosure may be prepared using any suitable method, such as conventional phosphotriester and phosphodiester methods or automated embodiments thereof so long as the primers are capable of hybridizing to the polynucleotides of interest. One method for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the method of the disclosure are complementary to each strand of nucleotide sequence to be amplified. The term "complementary" means that the primers must hybridize with their respective strands under conditions which allow the agent for polymerization to function. In other words, the primers that are complementary to the flanking sequences hybridize with the flanking sequences and permit amplification of the nucleotide sequence. Preferably, the 3' terminus of the primer that is extended has perfectly base paired complementarity with the complementary flanking strand.

Those of ordinary skill in the art will know of various amplification methodologies which can also be utilized to increase the copy number of target nucleic acid. The polynucleotides detected in the method of the disclosure can be further evaluated, detected, cloned, sequenced, and the like, either in solution or after binding to a solid support, by any method usually applied to the detection of a specific nucleic acid sequence such as another polymerase chain reaction, oligomer restriction (Saiki et al., Bio/Technology 3:1008-1012 (1985)), allele-specific oligonucleotide (ASO) probe analysis (Conner et al., Proc. Natl. Acad. Sci. USA 80: 278 (1983), oligonucleotide ligation assays (OLAs) (Landegren et al., Science 241:1077 (1988)), RNAse Protection Assay and the like. Molecular techniques for DNA analysis have been reviewed (Landegren et al, Science 242: 229-237 (1988)). Following DNA amplification, the reaction product may be detected by Southern blot analysis, without using radioactive probes. In such a process, for example, a small sample of DNA containing the polynucleotides obtained from the tissue or subject are amplified, and analyzed via a Southern blotting technique. The use of non-radioactive probes or labels is facilitated by the high level of the amplified signal. In one embodiment of the disclosure, one nucleoside triphosphate is radioactively labeled, thereby allowing direct visualization of the amplification product by autoradiography. In another embodiment, amplification primers are fluorescently labeled and run through an electrophoresis system. Visualization of amplified products is by laser detection followed by computer assisted graphic display, without a radioactive signal.

Simple visualization of a gel containing the separated products may be utilized to determine the presence of a disease, disorder or other physiological state. For example, staining of a gel to visualize separated polynucleotides, a number of stains are well known to those skilled in the art. However, other methods known to those skilled in the art may also be used, for example scanning densitometry, computer aided scanning and quantitation as well as others.

Thus, the methods described above can be used to invasively, minimally invasively or non-invasively obtain a sample from a subject suspected of having a disease, disorder, or physiological state to be analyzed. The polynucleotides can then be analyzed using methods such as, but not limited to, those described above. Any number of polynucleotides resulting from differential expression (e.g., cytokine levels) can be quantified by measuring their relative expression in the sample obtained and comparing these levels to a prior obtained sample. For example, the mRNA level(s) in a cell change when the production of proteins are either increased or reduced. Thus, a measurement of RNA, in particular mRNA, provides a monitor of event(s) occurring in a subject as a result of a local or a systemic response. It will be recognized that the techniques are capable of detecting any reaction, disorder, or disease so long as the biological factor is present in the sample.

The detectable label may be a radioactive label or may be a luminescent, fluorescent of enzyme label. Indirect detection processes typically comprise probes covalently labeled with a hapten or ligand such as digoxigenin (DIG) or biotin. Following the hybridization step, the target-probe duplex is detected by an antibody- or streptavidin-enzyme complex. Enzymes commonly used in DNA diagnostics are horseradish peroxidase and alkaline phosphatase. Direct detection methods include the use of fluorophor-labeled oligonucleotides, lanthanide chelate-labeled oligonucleotides or oligonucleotide-enzyme conjugates. Examples of fluorophor labels are fluorescein, rhodamine and phthalocyanine dyes.

Label detection will be based upon the type of label used in the particular assay. Such detection methods are known in the art. For example, radioisotope detection can be performed by autoradiography, scintillation counting or phosphor imaging. For hapten or biotin labels, detection is with an antibody or streptavidin bound to a reporter enzyme such as horseradish peroxidase or alkaline phosphatase, which is then detected by enzymatic means. For fluorophor or lanthanide-chelate labels, fluorescent signals may be measured with spectrofluorimeters with or without time-resolved mode or using automated microtitre plate readers. With enzyme labels, detection is by color or dye deposition (p-nitropheny phosphate or 5-bromo-4-chloro-3-indolyl phosphate/nitroblue tetrazolium for alkaline phosphatase and 3,3'-diaminobenzidine-$NiCl_2$ for horseradish peroxidase), fluorescence (e.g., 4-methyl umbelliferyl phosphate for alkaline phosphatase) or chemiluminescence (the alkaline phosphatase dioxetane substrates LumiPhos 530 from Lumigen Inc., Detroit Mich. or AMPPD and CSPD from Tropix, Inc.). Chemiluminescent detection may be carried out with X-ray or polaroid film or by using single photon counting luminometers.

Another technique, which may be used to analyze gene expression, includes multicomponent integrated systems, which miniaturize and compartmentalize processes such as PCR and capillary electrophoresis reactions in a single functional device. An example of such technique is disclosed in U.S. Pat. No. 5,589,136, the disclosure of which is incorporated herein by reference in its entirety, which describes the integration of PCR amplification and capillary electrophoresis in chips.

In another embodiment, polypeptides may be obtained from the sample by methods known to those of skill in the art. For example, gross preparations of cells obtained using the non-invasive techniques of the disclosure contain polypeptides. Alternatively, the polypeptides may be further isolated or purified using conventional means including preparative chromatography and immunological separations involving monoclonal or polyclonal antibodies. The polypeptides may then be characterized to indicate the presence of a dermatatic reaction.

The method for detecting a cytokine polypeptide in cells is useful for distinguishing and determining a change by measuring the level of a particular cytokine, for example IL-4, IL-8 and/or IL-13, in cells obtained from a subject suspected of having a dermatological reaction or stress reaction. The levels of such cytokines are indicative of a reaction when compared to a normal or standard cytokine polypeptide profile in a similar tissue. Thus, the expression pattern of a cytokine polypeptide will vary depending upon the type and degree of a disease, disorder, or physiological state such as stress state. In this regard, the sample obtained, as described herein, may be used as a source to isolate polypeptides. Measurements of a particular polypeptide serve as a method of identifying or monitoring a subject's mental or physiological state. The polypeptides may be quantified using methods known to those of skill in the art, for example by ELISA.

Monoclonal antibodies to a particular polypeptide, for example, IL-4, IL-8, IL-13 and others can be used in immunoassays, such as in liquid phase or bound to a solid phase carrier, to detect polypeptide associated with a disorder, diseases or reaction. In addition, the monoclonal antibodies in these immunoassays can be detectably labeled in various ways. Examples of types of immunoassays which can utilize monoclonal antibodies of the disclosure are competitive and non-competitive immunoassays in either a direct or indirect format. Examples of such immunoassays are the radioimmunoassay (RIA) and the sandwich (immunometric) assay. Detection of the polypeptide antigens using the monoclonal antibodies of the disclosure can be done utilizing immunoassays which are run in either the forward, reverse, or simultaneous modes, including immunohistochemical assays on physiological samples. Those of skill in the art will know, or can readily discern, other immunoassay formats without undue experimentation. In addition, there are a number of commercially available antibodies to cytokines of interest.

The term "immunometric assay" or "sandwich immunoassay" includes simultaneous sandwich, forward sandwich and reverse sandwich immunoassays. These terms are well understood by those skilled in the art. Those of skill will also appreciate that antibodies according to the disclosure will be useful in other variations and forms of assays which are presently known or which may be developed in the future. These are intended to be included within the scope of the disclosure.

Monoclonal antibodies can be bound to many different carriers and used to detect the presence of a cytokine polypeptide. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding monoclonal antibodies, or will be able to ascertain such using routine experimentation.

A cytokine polypeptide may be detected by the monoclonal antibodies when present in biological fluids and tissues. Any sample containing a detectable amount of cytokine can be used. A sample can be a liquid such as blood, serum and the like, or a solid or semi-solid such as tissues, skin sample, or, alternatively, a solid tissue such as those commonly used in histological diagnosis.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-cytokine immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays.

It has been found that a number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1-100 µg/µl) may be important, in order to maintain the proper sensitivity yet inhibit any unwanted interference by mutually occurring cross reactive proteins in the specimen.

Using the methods of the disclosure one can analyze changes in gene expression. Such changes can be indicative of any number of factors due to both internal factors and external factors (e.g., environmental factors). Changes in gene expression, as discussed more fully herein, are associated with various internal and external factors. Such factors include, but are not limited to, emotional states, mental stress, physical stress, oxidative stress, temperature, daylight hours, immune system changes, physical exertion, muscle building, inflammation, pain, drugs, placebo effects, genetic diseases, autoimmune diseases, depression, infection, distant intentionalities, developmental changes and the like. Psychological tools and mental activities such as meditation, visualization, and cognitive behavioral therapy are further examples of purely mental processes that correspond to changes in gene expression. In the disclosure, any mental state, emotional state, physical state, reaction, disease, or disorder that corresponds to an induction or reduction of transcription and polypeptide synthesis may be detected by the methods of the disclosure.

The methods and kits of the disclosure can be used as biofeedback to assist a subject in modulating a particular physical state or mental state the results in a detrimental gene expression profile or to diagnose an internal factor or external stimuli resulting in a detrimental gene expression profile. In another aspect, the methods and kits of the disclosure can be used to identify positive changes in gene expression profiles or identify various changes in gene expression important for temporal activities such as drug delivery, or as a biofeedback indicator. In yet a further aspect, the gene expression profile changes can be used to determine whether a test drug or other factor is providing a placebo effect. For example, uses of the methods and kits of the disclosure can provide data associated with gene expression relevant to a subject's interest.

The gene expression profiling provides an additional source of biofeedback. Biofeedback involves measuring a subject's bodily processes (here gene expression changes) and conveying such information to the subject in order to raise his or her awareness and conscious control of the related physiological activities or state of mind. By providing access to gene expression changes about which the user is generally unaware, the disclosure allows subjects to gain control over physical, emotional, and mental processes previously considered automatic.

For example, uses of the methods and kits of the disclosure can use data associated with gene pathways expression relevant to a subject's interest to assess a characteristic associate with changes in gene expression.

Muscle Building. Skeletal muscle exhibits plasticity through the dynamic regulation of specific genes in the muscle cells that sense change in muscle usage (Pilegaard, Osada et al. 2005) and activate transcription of select metabolic genes during recovery from exercise (Hildebrandt, Pilegaard et al. 2003). Resistance training in which muscle growth is achieved involves the break down and repair of skeletal muscle; this process involves transcription of inflammatory response genes that can be assessed in peripheral blood (Zieker, Zieker et al. 2005), (Whistler, Jones et al. 2005), (Connolly, Caiozzo et al. 2004). It has been documented that strenuous exercise not only induces pyrogenesis but also elicits mobilization and functional augmentation of neutrophils (Suzuki, Nakaji et al. 2002). The ability of neutrophils to generate proinflammatory cytokines is established (Cloutier, Ear et al. 2003). Accordingly, resting and muscle building states can be assessed by measuring transcription activation of genes related to muscle building. Applications include endurance and muscle training to determine appropriate times to exercise and rest.

Stress Reduction. Gene expression profiling in peripheral blood leukocytes may be used for the assessment the human stress responses (Rokutan, Morita et al. 2005), (Morita, Saito et al. 2005). Some candidate genes that have been evaluated in this regard in blood samples include IL-6 (Lutgendorf, Garand et al. 1999) and corticosteroid receptor-alpha (Bonifazi, Suman et al. 2006). The glucocorticoid receptor beta is expressed in human neutrophils (Strickland, Kisich et al. 2001) and may be relevant because glucocorticoids contribute fundamentally to the maintenance of basal and stress-related homeostasis. Monitoring changes in stress levels is an important factor in homeostatis. Applications include assessing the efficacy of stress reduction therapies and diagnosis, and prognosis of stress related diseases, disorders, and physiological states.

Immune System. Genes involved in cytokine secretion have been shown to be regulated in polymorphonuclear leukocytes, including IL-1 beta (Hendley, Steed et al. 1995), TNF-alpha, IL-8 and IL-1ra (Yoshimura, Hara et al. 1997), and specifically in neutrophils (Newburger, Subrahmanyam et al. 2000), including IL-1 receptor antagonist (Ethuin, Delarche et al. 2001). Evaluation of cytokine gene expression may prove useful in assessing the efficacy of therapies purported to boost the immune system, including mind-body practices such as Qi Gong (Jones 2001).

Pain. Opioid peptides are released from leukocytes, bind to opioid receptors on peripheral sensory neurons. In early inflammation, peripheral opioid-mediated antinociception is critically dependent on polymorphonuclear leukocytes and their recruitment by CXCR2 chemokines (Brack, Rittner et al. 2004). Likewise, polymorphonuclear leukocytes express the neuropeptide nociceptin and its receptor and have been postulated to mediate a novel dialogue pathway between neural and immune tissues (Fiset, Gilbert et al. 2003). Applications of the dynamic gene measurements of the disclosure include pain management therapies.

Oxidative Stress. Increased oxidative stress plays an important role in the pathophysiology of cardiovascular diseases such as hypertension, atherosclerosis and diabetes. A family of NADPH oxidases appears to be especially important for redox signaling including the prototypic Nox2 isoform-based NADPH oxidase, which was first characterized in neutrophils (Cave, Brewer et al. 2006). Genes encoding the high-affinity Fc gamma receptor for IgG (Fc gamma R-I, CD64) and two of the components of the phagocytic superoxide anion-generating system are expressed and modulated in human leukocytes (Amezaga, Bazzoni et al. 1992).

Monitoring Disease or Disorder States. It is possible to monitor various disease states and responsiveness to interventions through the gene expression profiles of neutrophils or other tissues. Supporting this possibility, increased expression of the serotonin transporter (5HTT) mRNA in peripheral leukocytes appears to be related with the pathophysiology of depression and its reduction after treatment may reflect the adaptive change induced by antidepressant medications (Iga, Ueno et al. 2005). Likewise, reduced glucocorticoid receptor alpha mRNA expression in peripheral blood cells might be trait-dependent and associated with the pathophysiology of mood disorders (Matsubara, Funato et al. 2006). Because neutrophils express NF-kappaB (Fialkow, Wang et al. 2007), the therapeutic potential of inhibition of the NF-kappaB pathway in the treatment of inflammation and cancer (Yamamoto and Gaynor 2001) might be assessed in neutrophils. Relevant to hypertension, leukocytes display differential expression of inflammation-related genes that is of importance in blood pressure control and treatment of blood pressure to normal values can be reflected in the expression profiles of these genes (Chon, Gaillard et al. 2004). Related to obesity, human polymorphonuclear leukocytes express the receptor for the satiety hormone leptin (Zarkesh-Esfahani, Pockley et al. 2004).

Emotions. Neuropeptides have been postulated as the biochemical substrates of emotion (Pert, Ruff et al. 1985). Investigation into this hypothesis may be facilitated by monitoring neutrophil gene expression because neuropeptides are expressed in these cells, for example vascular endothelial growth factor (Takahashi, Nakamura et al. 2005) and in peripheral blood lymphocytes, for example proopiomelanocortin (Stephanou, Fitzharris et al. 1991). Additionally, practices or psychopharmacological agents that produce changes in thought, mood, and perception may provide a model for identifying genetic pathways involved in states of mind because the effects are often more profound than those experienced normally. Examples of modalities that can be analyzed by the methods and kits of the disclosure include, but are not limited to, hypnosis (Rossi and Rossi 2007), lucid dreaming (Lequerica 1996), (Tholey 1983), trance states (Krippner 1997), (Frecska and Luna 2006) and psychotropic drugs.

Placebo. It may be possible to investigate the implicit involvement of the regulation of gene expression in the placebo response (see FIG. 1 above) because leukocytes produce and release opioid peptides to counteract inflammatory pain (Rittner, Labuz et al. 2006). The dynamic gene expression measurements of the disclosure can assist in evaluating clinical trial data and drug/therapeutic testing.

Distant Intentionality. Data reported in the literature indicate that gene expression is responsive to the influence of distant intentionality in the form of Qi Gong (Wardell and Engebretson 2001), (Yan, Shen et al. 2004). Should such an effect prove to be valid, evaluation of neutrophil gene expression would serve as a practical model for studying this and possibly for developing devices such as a "psychic switch."

Early Response Genes. Expression of the early response genes JunD and c-fos has been demonstrated in neutrophils (Cloutier, Ear et al. 2003). Because they encode proteins that modulate the transcription rates of numerous target genes (Sagar and Sharp 1993), this family of genes may be useful in examining all of the above topics.

Non-coding Genetic Material. Novel applications will likely become evident as the function of non-protein-coding fraction of the genome, such as non-coding DNA (Ponting and Lunter 2006), non-coding RNAs (Qi, Li et al. 2006) and microRNAs (Huppi, Volfovsky et al. 2007), become better understood.

It is also contemplated that the gene expression provides may be transmitted to a remote location for analysis. For example, changes in a detectable signal related to gene expression from a first time and a second time are communicated to a remote location for analysis.

The digital representation of the detectable signal is transmittable over any number of media. For example, such digital data can be transmitted over the Internet in encrypted or in publicly available form. The data can be transmitted over phone lines, fiber optic cables or various air-wave frequencies. The data are then analyzed by a central processing unit at a remote site, and/or archived for compilation of a data set that could be mined to determine, for example, changes with respect to historical mean "normal" values of a genetic expression profile of a subject.

Embodiments of the disclosure include systems (e.g., internet based systems); particularly computer systems which store and manipulate the data corresponding to the detectable signal obtained an expression profile. As used herein, "a computer system" refers to the hardware components, software components, and data storage components used to analyze the digital representative of an expression profile or plurality of profiles. The computer system typically includes a processor for processing, accessing and manipulating the data. The processor can be any well-known type of central processing unit.

Typically the computer system is a general purpose system that comprises the processor and one or more internal data storage components for storing data, and one or more data retrieving devices for retrieving the data stored on the data storage components. A skilled artisan can readily appreciate that any one of the currently available computer systems are suitable.

In one particular embodiment, the computer system includes a processor connected to a bus which is connected to a main memory (preferably implemented as RAM) and one or more internal data storage devices, such as a hard drive and/or other computer readable media having data recorded thereon. In some embodiments, the computer system further includes one or more data retrieving device for reading the data stored on the internal data storage devices.

The data retrieving device may represent, for example, a floppy disk drive, a compact disk drive, a magnetic tape drive, or a modem capable of connection to a remote data storage system (e.g., via the internet) and the like. In some embodiments, the internal data storage device is a removable computer readable medium such as a floppy disk, a compact disk, a magnetic tape, and the like, containing control logic and/or data recorded thereon. The computer system may advantageously include or be programmed by appropriate software for reading the control logic and/or the data from the data storage component once inserted in the data retrieving device.

In one embodiment, a kit for gene expression profiling comprises the reagents and instructions necessary for the gene expression profiling. Thus, for example, the reagents may include primers, enzymes, and other reagents for the preparation, detection, and quantitation of mRNA or cDNA. Table 1 provides a number of genes that can be monitored using the methods of the disclosure. Primers and probes can be readily identified from the sequences associated with the accession numbers in Table 1. In addition to the primers, probes or oligonucleotide chips, reagents such as dinucleotide triphosphate comprising dinucleotide triphosphates (e.g., dATP, dGTP, dCTP, and dTTP), reverse transcriptase, and a thermostable DNA polymerase can be included in the kit. Additionally buffers, inhibitors and activators used for the RT-PCR process are suitable reagents for inclusion in the kit embodiment. Once the cDNA has been sufficiently amplified to a specified end point, the cDNA sample must be prepared for detection and quantitation. One method contemplated for detection of polynucleotides is fluorescence spectroscopy using fluorescent moieties or labels that are suited to fluorescence spectroscopy are desirable for labeling polynucleotides and may also be included in reagents of the kit embodiment.

In another embodiment, a kit for protein expression profiling comprises the reagents and instructions necessary for protein expression profiling of a polypeptide panel. Thus, in this embodiment, the kit for protein expression profiling includes supplying an antibody panel based on a panel of targeted polypeptides from a biological sample. One embodiment contemplated for such a panel includes the antibody panel bound to a solid support. Additionally, the reagents included with the kit for protein expression profiling may use a second antibody having specificity to some portion of the bound polypeptide. Such a second antibody may be labeled with molecules useful for detection and quantitation of the bound polypeptides.

The kits of the disclosure can comprise integrated systems having a plurality of components operably linked to facilitate gene expression detection (e.g., microfluidic systems in combination with oligonucleotide/DNA chips can be used). These systems comprise a pattern of microchannels designed onto a glass, silicon, quartz, or plastic wafer included on a microchip. The movements of the samples are controlled by electric, electroosmotic or hydrostatic forces applied across different areas of the microchip. The microfluidic system may integrate nucleic acid amplification, microsequencing, capillary electrophoresis and a detection method such as laser-induced fluorescence detection. integrated system itself, a component thereof, or data representative of the gene expression profile can be transmitted to a laboratory or remote location in physical form or digital form.

Generally, the methods and kits of the disclosure are designed to obtain at least two different expression profiles at different times from the same subject, quantify changes in the expression profile (either in a salon based environment, clinical environment or remotely), and identifying/outputting those changes to the subject or clinician. The subject or clinician can then associate the changes in expression profile with a particular environmental factor (e.g., stress) or a disease or disorder, or, in the case of a clinical trial, with a placebo effect.

The oligonucleotides in a kit of the disclosure may also be immobilized on or synthesized on a solid surface such as a microchip, bead, or glass slide (see, e.g., WO 98/20020 and WO 98/20019). Such immobilized oligonucleotides may be used in a variety of detection assays, including but not limited to, probe hybridization and polymerase extension assays. Immobilized oligonucleotides useful in practicing the disclosure may comprise an ordered array of oligonucleotides designed to rapidly screen a nucleic acid sample.

Kits of the disclosure may also contain other components such as hybridization buffer (e.g., where the oligonucleotide probes) or dideoxynucleotide triphosphates (ddNTPs; e.g., for primer extension). In one embodiment, the set of oligonucleotides consists of primer-extension oligonucleotides. The kit may also contain a polymerase and a reaction buffer optimized for primer-extension mediated by the polymerase. Kits may also include detection reagents, such as biotin- or fluorescent-tagged oligonucleotides or ddNTPs and/or an enzyme-labeled antibody and one or more substrates that generate a detectable signal when acted on by the enzyme. It is also contemplated that the above described methods and compositions of the disclosure may be utilized in combination with other biomarker techniques.

The kit may also have containers containing nucleotides for amplification of or hybridization to the target nucleic acid sequence which may or may not be labeled, or a container comprising a reporter, such as a biotin-binding protein, such as avidin or streptavidin, bound to a reporter molecule, such as an enzymatic, florescent, or radionuclide label. The term "detectably labeled deoxyribonucleotide" refers to a means for identifying deoxyribonucleotide. For example, the detectable label may be a radiolabeled nucleotide or a small molecule covalently bound to the nucleotide where the small molecule is recognized by a well-characterized large molecule. Examples of these small molecules are biotin, which is bound by avidin, and thyroxin, which is bound by anti-thyroxin antibody. Other methods of labeling are known to those of ordinary skill in the art, including enzymatic, fluorescent compounds, chemiluminescent compounds, phosphorescent compounds, and bioluminescent compounds.

Kits of the disclosure may contain other components such as fixative agents. In one embodiment, fixative agent is formaldehyde or paraformaldehyde. In yet another embodiment, fixative agent is alcohol.

The invention is not to be limited in scope by the specific examples provided for below, which are intended as single illustrations of individual aspects of the invention and functionally equivalent methods and components are within the scope of the invention.

EXAMPLE

A saliva sample was obtained from a subject before starting a muscular resistance training exercise. The subject rinsed their mouth with an osmotically balanced solution (Hank's Balanced Salt Solution), and then ejected rinse-saliva into a collection device. The saliva sample was treated with formaldehyde solution at a concentration of 37% W/W and at a final concentration of 2.3%. Samples were stored at 4° C. Neutrophils were then separated from epithelial cells by filtration and sent to a laboratory for gene expression profiling. The subject then performed muscular resistance training exercise for a period of 30 minutes. A second saliva sample was obtained from the subject 120 minutes after the subject had started the muscular resistance training exercise. The second saliva sample was treated the same way and the collected neutrophils were sent to a laboratory for gene expression profiling.

Figure 1B:
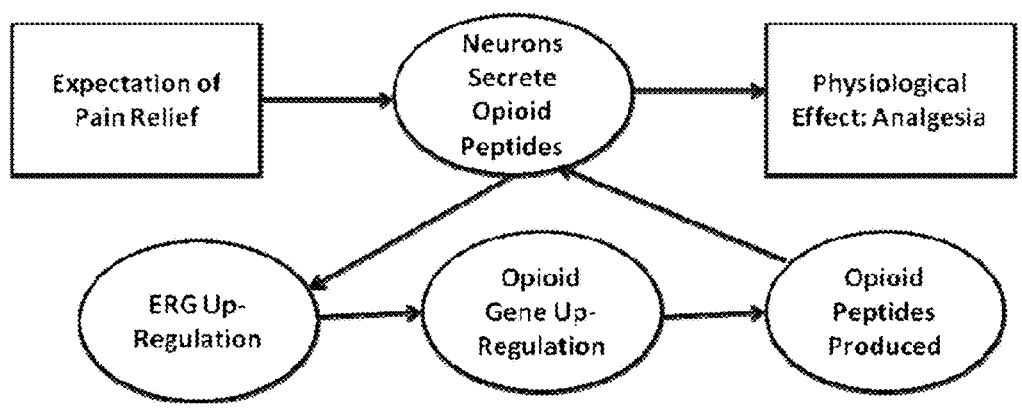
FIG. 1B shows an example of a biological response and gene expression change.

A small number of oral neutrophils from two separate samples (designated #3 and #5) were used as a source of mRNA. FIG. 1A demonstrates global PCR amplification of mRNA yielded cDNA of sufficiently high quality for gene expression analysis as determined by gel electrophoresis and subsequent hybridization to microarrays.

The data in Table 1 demonstrates a change in gene profiling of a subject, identifying the genes present in the subject's sputum, which is indicative of the subject's physiological state after muscular resistance training exercise.

TABLE 1

| Gene# | Name | UniProt/tremble | RefSeq accession no. | Change value |
|---|---|---|---|---|
| 3 | IL1B: (IL1B) INTERLEUKIN-1 BETA PRECURSOR (IL-1 BETA) (CATABOLIN). | P01584 Q7RU01 Q96HE5 Q9UCT6 | NM_000576 | |
| 5 | IL2: (IL2 OR IL-2) INTERLEUKIN-2 PRECURSOR (IL-2) (T-CELL GROWTH FACTOR) (TCGF) (ALDESLEUKIN). | P01585 Q13169 P60568 | NM_000586 | |
| 7 | IL3: (IL3 OR IL-3 OR CSFMU) INTERLEUKIN-3 PRECURSOR (IL-3). | P08700 | NM_000588 | |
| 14 | IL5: (IL5 OR IL-5) INTERLEUKIN-5 PRECURSOR (IL-5). | P05113 Q13840 | NM_000879 | |
| 16 | IL7: (IL7 OR IL-7) INTERLEUKIN-7 PRECURSOR (IL-7). | P13232 | NM_000880 | |
| 18 | IL8_HUMAN: (IL8) INTERLEUKIN-8 PRECURSOR (IL-8) (CXCL8). | P10145 Q6FGF6 Q6LAE6 Q96RG6 Q9C077 | NM_000584 | |

TABLE 1-continued

| Gene# | Name | UniProt/tremble | RefSeq accession no. | Change value |
|---|---|---|---|---|
| 20 | IL9: (IL9) INTERLEUKIN-9 PRECURSOR (IL-9) (T-CELL GROWTH FACTOR P40). | P15248 | NM_000590 | |
| 22 | IL10: (IL10 OR IL-10) INTERLEUKIN-10 PRECURSOR (IL-10) (CYTOKINE SYNTHESIS INHIBITORY FACTOR) (CSIF). | P22301 | NM_000572 | |
| 24 | IL11: (IL11) INTERLEUKIN-11 PRECURSOR (IL-11) (ADIPOGENESIS INHIBITORY FACTOR) (AGIF) (OPRELVEKIN). | P20809 | NM_000641 | |
| 26 | IL12A: (IL12A OR NKSF1) INTERLEUKIN-12 ALPHA CHAIN PRECURSOR (IL-12A) (NKSF1). | P29459 Q96QZ1 | NM_000882 | |
| 28 | IL12B: (IL12B OR NKSF2) INTERLEUKIN-12 BETA CHAIN PRECURSOR (IL-12B) (NKSF2). | P29460 | NM_002187 | |
| 30 | IL13: (IL13 OR NC30 OR IL-13) INTERLEUKIN-13 PRECURSOR (IL-13) (T-CELL ACTIVATION PROTEIN P600). | P35225 O43644 | NM_002188 | |
| 32 | TXLN: (TXLN) TAXILIN (IL14). | P40222 Q8N2Y3 Q66K62 Q86T54 Q86T85 Q86T86 Q86Y86 Q86YW3 | NM_175852 | |
| 33 | IL15_1: (IL15) INTERLEUKIN-15 PRECURSOR (IL-15). | P40933 Q93058 O43512 O00440 Q9UBA3 | NM_000585 NM_172174 | |
| 35 | IL16: (IL16) INTERLEUKIN-16 PRECURSOR (IL-16) (LYMPHOCYTE CHEMOATTRACTANT FACTOR) (LCF). | Q14005 Q16435 Q9UP18 | NM_004513 NM_172217 | |
| 37 | IL17: (IL17 OR CTLA8 OR IL17A) INTERLEUKIN-17 PRECURSOR (IL-17). | Q16552 | NM_002190 | 0.04/—% |
| 39 | IL18: (IL18 OR IGIF) INTERLEUKIN-18 PRECURSOR (IL-18). | Q14116 O75599 | NM_001562 | |
| 41 | TNF: (TNF OR TNFSF2 OR TNFA) TUMOR NECROSIS FACTOR PRECURSOR (TNF-ALPHA) (CACHECTIN). | P01375 O43647 Q9P1Q2 Q9UIV3 | NM_000594 | |
| 43 | TNFR1: (TNFRSF1A OR TNFR1 OR TNFAR OR TNFR-1). | P19438 | NM_001065 | |
| 45 | IFNG: (IFNG) INTERFERON GAMMA PRECURSOR (IFN-GAMMA) (IMMUNE INTERFERON). | P01579 | NM_000619 | |
| 47 | ACTA2: (ACTA2 OR ACTSA OR ACTVS) AORTIC SMOOTH MUSCLE (ALPHA-ACTIN 2). | P62736 | NM_001613 | |
| 49 | TUBA_HUMAN: ((K-ALPHA-1) AND (TUBA3) AND (TUBA6)). | P68363 Q9BQE3 Q71U36 | NM_006009 NM_006082 NM_032704 | |
| 55 | TUBB_HUMAN: (TUBB OR TUBB5) TUBULIN BETA CHAIN. | P07437 | NM_178014 | |
| 57 | TNFSF13: (TNFSF13 OR APRIL OR TALL2 OR ZTNF2) TUMOR NECROSIS FACTOR LIGAND SUPERFAMILY MEMBER 13 | O75888 Q96HV6 Q9P1M8 Q9P1M9 | NM_003808 NM_172087 NM_172088 NM_172089 | |
| 65 | TRAIN: (TNFRSF19 OR TROY OR TAJ). | Q9NZV2 Q9BXZ9 Q9BY00 Q9NS68 | NM_018647 NM_148957 | |
| 77 | TNFRSF6: (TNFRSF6 OR APT1 OR FAS OR FAS1 OR PT1). | P25445 Q6SSE9 Q14293 Q14294 Q14295 Q14292 Q16652 | NM_000043 NM_152871 NM_152872 NM_152873 NM_152874 NM_152875 NM_1 | |
| 79 | TNFSF6: (TNFSF6 OR FASL OR APT1LG1 OR GLD). | P48023 Q9BZP9 | NM_000639 | |
| 83 | TNFSF13B: (TNFSF13B OR TALL1 OR BLYS OR BAFF OR ZTNF4) | Q9Y275 | NM_006573 | |
| 97 | EDA_1: (ED1 OR EDA OR TA) ECTODYSPLASIN A (ECTODERMAL DYSPLASIA PROTEIN) (EDA PROTEIN) (TABBY PROTEIN). | Q5JUM7 Q9UP77 Q9Y6L0 Q9Y6L1 Q9Y6L2 Q9Y6L3 Q9Y6L4 Q92838 O75910 | NM_001005609 NM_001005610 NM_001005611 NM_001005612 NM_001005613 | |
| 99 | TNFSF10: (TNFSF10 OR TRAIL OR APO2L). | P50591 | NM_003810 | |
| 101 | TNFRSF10A_HUMAN: (TRAILR1 OR TNFRSF10A OR DR4 OR APO2)(TRAIL RECEPTOR-1) | O00220 Q96E62 | NM_003844 | |
| 102 | TNFRSF10B: (TNFRSF10B OR TRAILR2 OR DR5 OR TRICK2 OR KILLER OR ZTNFR9) (TRAIL RECEPTOR-2). | O15508 O14763 O15531 O15517 O14720 Q9BVE0 | NM_003842 NM_147187 | |
| 104 | TNFRSF10D_HUMAN: (TNFRSF10D OR DCR2 OR TRAILR4 OR TRUNDD)(TRAIL RECEPTOR-4) | Q9UBN6 Q9Y6Q4 | NM_003840 | |
| 105 | TNFRSF25: (TNFRSF25 OR TNFRSF12 OR WSL1 OR WSL OR APO3 OR DR3 OR DDR3 OR TRAMP)(WSL PROTEIN) | Q93038 Q93036 Q93037 Q92983 P78515 Q99831 Q99722 P78507 Q99830 O | NM_003790 NM_148965 NM_148966 NM_148967 NM_148970 | |
| 106 | TNFSF11: (TNFSF11 OR RANKL OR TRANCE OR OPGL) TUMOR NECROSIS FACTOR LIGAND SUPERFAMILY MEMBER 11 (TRANCE) | O14788 O14723 Q96Q17 Q9P2Q3 | NM_003701 NM_033012 | |
| 108 | TNFSF12: (TNFSF12 OR APO3L OR DR3LG) TUMOR NECROSIS FACTOR LIGAND SUPERFAMILY MEMBER 12. | O43508 Q8WUZ7 | NM_003809 NM_153012 | |
| 196 | TNFRSF9: (TNFRSF9 OR ILA) 4-1BB LIGAND RECEPTOR PRECURSOR (T-CELL ANTIGEN 4-1BB HOMOLOG). | Q07011 | NM_001561 | |
| 200 | TNFSF9: (TNFSF9 OR LY63L OR CD137L OR CD157L) TUMOR NECROSIS FACTOR LIGAND SUPERFAMILY MEMBER 9. | P41273 | NM_003811 | |
| 218 | TNFRSF8: (TNFRSF8 OR CD30) TUMOR NECROSIS FACTOR RECEPTOR SUPERFAMILY MEMBER 8 PRECURSOR (CD30L RECEPTOR). | P28908 | NM_001243 NM_152942 | 2.80/—% |

TABLE 1-continued

| Gene# | Name | UniProt/tremble | RefSeq accession no. | Change value |
|---|---|---|---|---|
| 220 | TNFSF8: (TNFSF8 OR CD30LG OR CD30L) TUMOR NECROSIS FACTOR LIGAND SUPERFAMILY MEMBER 8. | P32971 O43404 | NM_001244 | |
| 222 | TNFRSF5: (TNFRSF5 OR CD40) TUMOR NECROSIS FACTOR RECEPTOR SUPERFAMILY MEMBER 5 PRECURSOR (CD40L RECEPTOR). | P25942 Q9BYU0 | NM_001250 NM_152854 | 1.01/3% |
| 224 | TNFSF5: (TNFSF5 OR CD40LG OR CD40L OR TRAP) TUMOR NECROSIS FACTOR LIGAND SUPERFAMILY MEMBER 5 (CD40 LIGAND). | P29965 | NM_000074 | |
| 229 | HVEM: (TNFRSF14 OR HVEM) TUMOR NECROSIS FACTOR RECEPTOR SUPERFAMILY MEMBER 14 PRECURSOR (TR2). | Q96J31 Q8WXR1 Q92956 Q9UM65 | NM_003820 | |
| 233 | TNFSF14: (TNFSF14 OR LIGHT OR HVEML) TUMOR NECROSIS FACTOR LIGAND SUPERFAMILY MEMBER 14 | Q96LD2 Q8WVF8 O43557 O75476 | NM_003807 NM_172014 | |
| 236 | TNFRSF11B: (TNFRSF11B OR OPG OR OCIF) OSTEOPROTEGERIN PRECURSOR. | O00300 O60236 Q53FX6 Q9UHP4 | NM_002546 | |
| 238 | DCR3_HUMAN: (TNFRSF6B OR DCR3 OR TR6) TUMOR NECROSIS FACTOR RECEPTOR SUPERFAMILY MEMBER 6B PRECURSOR (M68). | O95407 | NM_003823 NM_032945 | |
| 241 | TNFSF4: (TNFSF4 OR TXGP1) OX40 LIGAND (OX40L) (GLYCOPROTEIN GP34) (CD252 ANTIGEN). | P23510 Q9HCN9 | NM_003326 | |
| 243 | TNFRSF11A: (TNFRSF11A OR RANK) TUMOR NECROSIS FACTOR RECEPTOR SUPERFAMILY MEMBER 11A PRECURSOR (CD265 ANTIGEN). | Q9Y6Q6 | NM_003839 | |
| 247 | TNFB: (LTA OR TNFSF1 OR TNFB) LYMPHOTOXIN-ALPHA PRECURSOR (LT-ALPHA) (TNF-BETA). | P01374 Q9UKS8 Q8N4C3 | NM_000595 | |
| 249 | TNFC: (LTB OR TNFC OR TNFSF3) LYMPHOTOXIN-BETA (LT-BETA) (TUMOR NECROSIS FACTOR C) (TNF-C) | Q06643 P78370 Q99761 | NM_002341 NM_009588 | |
| 251 | TNFRSF1B: (TNFRSF1B OR TNFR2 OR TNFBR OR TNFR-2) (ETANERCEPT). | P20333 Q16042 Q9UIH1 Q6YI29 | NM_001066 | |
| 253 | LTBR: (LTBR OR TNFCR OR TNFRSF3) LYMPHOTOXIN-BETA RECEPTOR PRECURSOR. | P36941 | NM_002342 | |
| 301 | CYPA: (PPIA OR CYPA) CYCLOPHILIN 1 PEPTIDYL-PROLYL CIS-TRANS ISOMERASE A | P62937 Q6IBU5 Q3KQW3 | NM_021130 | |
| 317 | CSF3R: (CSF3R OR GCSFR) (CD114 ANTIGEN). | Q99062 | NM_000760 NM_156038 NM_156039 NM_172313 | |
| 319 | CSF1R: (CSF1R OR CSFMR OR FMS) MACROPHAGE COLONY STIMULATING FACTOR I RECEPTOR PRECURSOR (CSF-1-R) | P07333 Q6LDW5 Q6LDY4 | NM_005211 | |
| 321 | CSF2RA: ((CSF2RAX OR CSF2RA OR CSF2R OR CSF2RX) AND (CSF2RAY OR CSF2RA OR CSF2R OR CSF2RY)). | P15509 Q14429 Q14430 Q14431 O00207 Q16564 | NM_006140 NM_172245 NM_172246 NM_172247 NM_172249 | |
| 322 | KIT: (KIT OR SL) MAST/STEM CELL GROWTH FACTOR RECEPTOR PRECURSOR (EC 2.7.1.112) (SCFR). | P10721 Q9UM99 | NM_000222 | |
| 324 | IFNGR1: (IFNGR1 OR IFNGR) INTERFERON-GAMMA RECEPTOR ALPHA CHAIN PRECURSOR (CDW119) (CD119). | P15260 | NM_000416 | |
| 326 | IL1R1: (IL1R1 OR IL1RA OR IL1R) INTERLEUKIN-1 RECEPTOR, TYPE I PRECURSOR (IL-1R-1)(P80) (ANTIGEN CD121A). | P14778 | NM_000877 | |
| 328 | IL1R2: (IL1R2 OR IL1RB) INTERLEUKIN-1 RECEPTOR, TYPE II PRECURSOR (IL-1R-2) (IL-1R-BETA) (ANTIGEN CDW121B). | P27930 Q9UE68 | NM_004633 NM_173343 | |
| 330 | IL2RB: (IL2RB) INTERLEUKIN-2 RECEPTOR BETA CHAIN PRECURSOR (IL-2 RECEPTOR) (P70-75). | P14784 | NM_000878 | 1.48/41% |
| 332 | IL3RA: ((IL3RAX OR IL3RA OR IL3R OR IL3RX) AND (IL3RAY OR IL3RA OR IL3R OR IL3RY)) (CD123 ANTIGEN). | P26951 | NM_002183 | |
| 333 | IL4R: (IL4R OR IL4RA OR 582J2.1) INTERLEUKIN-4 RECEPTOR ALPHA CHAIN PRECURSOR (IL-4R-ALPHA) (CD124 ANTIGEN). | P24394 Q96P01 Q9H181 Q9H182 Q9H183 Q9H184 Q9H185 Q9H186 Q9H187 Q | NM_000418 | |
| 335 | IL5RA: (IL5RA OR IL5R) INTERLEUKIN-5 RECEPTOR ALPHA CHAIN PRECURSOR (IL-5R-ALPHA) (CD125 ANTIGEN). | Q01344 Q6ISX9 | NM_000564 NM_175724 NM_175725 NM_175726 NM_175727 NM_175728 | |
| 337 | IL6R: (L6RA OR IL6R) INTERLEUKIN-6 RECEPTOR ALPHA CHAIN PRECURSOR (IL-6R-ALPHA) (CD126 ANTIGEN) (IL-6R 1). | P08887 Q53EQ7 Q5FWG2 Q5VZ23 Q16202 | NM_000565 NM_181359 | |
| 339 | IL7R: (IL7R) INTERLEUKIN-7 RECEPTOR ALPHA CHAIN PRECURSOR (IL-7R-ALPHA) (CDW127) (CD127 ANTIGEN). | P16871 Q6SV45 Q9UPC1 | NM_002185 | |
| 343 | IL6ST: (IL6ST) INTERLEUKIN-6 RECEPTOR BETA CHAIN PRECURSOR (IL-6R-BETA)(CD130 ANTIGEN). | P40189 Q9UQ41 | NM_002184 NM_175767 | |
| 345 | CSF2RB: (CSF2RB OR IL5RB OR IL3RB OR RIL-3ROR CSF2RB1 OR AIC2B OR IL3RB1) | P32927 | NM_000395 | |
| 347 | IL2RG: (IL2RG) CYTOKINE RECEPTOR COMMON GAMMA CHAIN PRECURSOR (GAMMA-C)(P64) (CD132 ANTIGEN). | P31785 | NM_000206 | |
| 349 | FLT3: (FLT3 OR STK1 OR FLT-3 OR FLK-2) FL CYTOKINE RECEPTOR PRECURSOR (CD135 ANTIGEN). | P36888 Q13414 | NM_004119 | |

TABLE 1-continued

| Gene# | Name | UniProt/trembl | RefSeq accession no. | Change value |
|---|---|---|---|---|
| 351 | MST1R: (MST1R OR RON OR STK) MACROPHAGE-STIMULATING PROTEIN RECEPTOR PRECURSOR(CD136 ANTIGEN). | Q04912 | NM_002447 | |
| 355 | PDGFRA: (PDGFRA) ALPHA PLATELET-DERIVED GROWTH FACTOR RECEPTOR PRECURSOR (CD140A ANTIGEN). | P16234 Q96KZ7 | NM_006206 | |
| 357 | PDGFRB: (PDGFRB OR PDGFR) BETA PLATELET-DERIVED GROWTH FACTOR RECEPTOR PRECURSOR(CD140B ANTIGEN). | P09619 Q8N5L4 | NM_002609 | |
| 361 | F3: (F3 OR CF3 OR CF-3) TISSUE FACTOR PRECURSOR (TF)(THROMBOPLASTIN) (CD142 ANTIGEN). | P13726 Q6FHG2 | NM_001993 | |
| 420 | TNFSF7: (TNFSF7 OR CD70 OR CD27LG OR CD27L) (CD27 LIGAND) (CD27-L) (CD70 ANTIGEN). | P32970 Q96J57 | NM_001252 | |
| 491 | IL2RA: (IL2RA OR IL2R) INTERLEUKIN-2 RECEPTOR ALPHA CHAIN PRECURSOR(P55) (TAC ANTIGEN) (CD25 ANTIGEN) | P01589 | NM_000417 | |
| 495 | TNFRSF7: (TNFRSF7 OR CD27) (CD27L RECEPTOR) ((T14). | P26842 | NM_001242 | |
| 670 | CXCR3: (CXCR3 OR GPR9 OR CMKAR3) C-X-C CHEMOKINE RECEPTOR TYPE 3 (CXC-R3) (CXCR-3) (CKR-L2) (CD183 ANTIGEN). | P49682 Q7Z710 Q9P2T4 Q9P2T5 O15185 | NM_001504 | |
| 683 | CCR3: (CCR3 OR CMKBR3 OR CMKBR1L2) C-C CHEMOKINE RECEPTOR TYPE 3(CC-CKR-3) (CCR-3)(CKR3) (MIP-1 ALPHA RL2). | P51677 Q15748 Q86WD2 Q9ULY8 | NM_001837 NM_178329 | |
| 685 | CCR4: (CCR4 OR CMKBR4) C-C CHEMOKINE RECEPTOR TYPE 4 (C-C CKR-4) (CC-CKR-4) (CCR-4) (CCR4) (K5-5) (CD194 ANTIGEN). | P51679 Q9ULY6 Q9ULY7 | NM_005508 | |
| 994 | CCR9: (CCR9 OR CMKBR9 OR GPR28 OR CMKBR10) C-C CHEMOKINE RECEPTOR TYPE 9(CC-CKR-9) (CCR-9). | P51686 Q4VBM3 Q549E0 Q9UQQ6 | NM_006641 NM_031200 | |
| 1009 | CCR10: (CCR10 OR GPR2) C-C CHEMOKINE RECEPTOR TYPE 10 (C-C CKR-10) (CC-CKR-10) (CCR-10). | P46092 Q6T7X2 Q9NZG2 | NM_016602 | 0.02/63% |
| 1016 | XCR1: (CCXCR1 OR XCR1 OR GPR5) CHEMOKINE XC RECEPTOR 1 (XC CHEMOKINE RECEPTOR 1). | P46094 | NM_001024644 NM_005283 | |
| 1348 | PDGA: (PDGFA OR RPA1 OR PDGF1) PDGA PLATELET-DERIVED GROWTH FACTOR, A CHAIN PRECURSOR(PDGF-1) | P04085 | NM_002607 NM_033023 | |
| 1350 | PDGB: (PDGFB OR C-SIS OR PDGF2 OR SIS) PLATELET-DERIVED GROWTH FACTOR, B CHAIN PRECURSOR (PDGF B-CHAIN)(C-SIS). | P01127 P78431 Q9UF23 | NM_002608 NM_033016 | |
| 1352 | PLGF: (PGF OR PLGF) PLACENTA GROWTH FACTOR PRECURSOR (PLGF-1/PLGF-2). | P49763 Q9BV78 Q9Y6S8 Q07101 | NM_002632 | |
| 1525 | PRF1: (PRF1 OR PFP) PERFORIN 1 PRECURSOR (P1) (LYMPHOCYTE PORE FORMING PROTEIN) (PFP) (CYTOLYSIN) | P14222 Q86WX7 | NM_005041 | |
| 1695 | GRO1_HUMAN: (CXCL1 OR SCYB1 OR GRO1 OR GROA OR GRO OR MGSA OR GRO-ALPHA) (NAP-3). | P09341 | NM_001511 | |
| 1697 | CXCL3_HUMAN: (CXCL3 OR GRO3 OR SCYB3 OR GROG). | P19876 | NM_002090 | |
| 2000 | IL4: (IL4 OR IL-4) INTERLEUKIN-4 PRECURSOR (IL-4) (B-CELL STIMULATORY FACTOR 1). | P05112 Q14630 | NM_000589 NM_172348 | |
| 2009 | CXCR4: (CXCR4 OR LESTR OR CMKAR4 OR SDF1R) C-X-C CHEMOKINE RECEPTOR TYPE 4 (CXC-R4) | P61073 P30991 P56438 Q9UKN2 O60835 | NM_003467 | |
| 2011 | CCR1: (CCR1 OR CMKBR1 OR CMKR1) C-C CHEMOKINE RECEPTOR TYPE 1 (C-C CKR-1) (CC-CKR-1). | Q86VA9 P32246 | NM_001295 | |
| 2015 | CCR6: (CCR6 OR CMKBR6 OR STRL22 OR GPR29 OR CKRL3) C-C CHEMOKINE RECEPTOR TYPE 6 (C-C CKR-6). | P51684 Q92846 P78553 | NM_004367 NM_031409 | |
| 2017 | CCR7: (CKR7 OR CMKBR7 OR EBI1 OR EVI1 OR EBI1H) C-C CHEMOKINE RECEPTOR TYPE 7 PRECURSOR (C-C CKR-7). | P32248 | NM_001838 | |
| 2019 | CCR8: (CCR8 OR CMKBR8 OR CKRL1 OR TER1) C-C CHEMOKINE RECEPTOR TYPE 8 (C-C CKR-8)(CDW198 ANTIGEN). | Q3KNQ8 P51685 | NM_005201 | |
| 2073 | CX3CR1: (CX3CR1 OR GPR13) CX3C CHEMOKINE RECEPTOR 1 (C-X3-C CKR-1) (CX3CR1) (CMK-BRL-1) (CMKBLR1). | P49238 | NM_001337 | |
| 2211 | GAPD: (GAPD) GLYCERALDEHYDE 3-PHOSPHATE DEHYDROGENASE, LIVER (GAPDH). | P04406 P00354 | NM_002046 | 0.04/—% |
| 2517 | SPP1: (SPP1 OR OPN) OSTEOPONTIN PRECURSOR (BONE SIALOPROTEIN 1) (SPP-1) (NEPHROPONTIN) | P10451 Q8NBK2 Q96IZ1 Q15681 Q15682 Q15683 | NM_000582 NM_001040058 NM_001040060 | |
| 2547 | TGFA: (TGFA) TRANSFORMING GROWTH FACTOR ALPHA PRECURSOR (TGF-ALPHA) (EGF-LIKE TGF) (ETGF) (TGF TYPE 1) (TGFA55). | P01135 Q15577 | NM_003236 | |
| 2936 | IL6: (IL6 OR IFNB2 OR IL-6) INTERLEUKIN-6 PRECURSOR (IL-6)(BSF-2) (INTERFERON BETA-2) | Q9UCU2 Q9UCU3 Q9UCU4 P05231 | NM_000600 | |
| 2970 | IL1A: (IL1A) INTERLEUKIN-1 ALPHA PRECURSOR (IL-1 ALPHA) (HEMATOPOIETIN-1). | Q7RU02 P01583 | NM_000575 | |
| 3018 | HPRT: (HPRT1 OR HPRT) HYPOXANTHINE-GUANINE PHOSPHORIBOSYLTRANSFERASE (EC 2.4.2.8) (HGPRT). | P00492 | NM_000194 | |
| 3616 | MAF_1: (MAF OR MAF2) TRANSCRIPTION FACTOR MAF (PROTO-ONCOGENE C-MAF). | Q9UP93 O75444 | NM_001031804 | 1.04/2% |
| 3716 | FOXP3: (FOXP3 OR IPEX) FORKHEAD BOX PROTEIN P3 (ZINC FINGER PROTEIN JM2) (SCURFIN). | O60827 Q9BZS1 Q4ZH51 | NM_014009 | |
| 3804 | GRO2_HUMAN: (CXCL2 OR GRO2 OR SCYB2 OR GROB OR MIP2A). | P19875 Q9UPB8 | NM_002089 | |

TABLE 1-continued

| Gene# | Name | UniProt/tremble | RefSeq accession no. | Change value |
|---|---|---|---|---|
| 4025 | SOCS6: (SOCS6 OR SOCS4 OR CIS4) SUPPRESSOR OF CYTOKINE SIGNALING 6 (SOCS-6) | O14544 | NM_004232 | 0.99/2% |
| 4027 | SOCS5: (SOCS5 OR CISH5 OR CIS6 OR CISH6 OR KIAA0671) CYTOKINE INDUCIBLE SH2-CONTAINING PROTEIN 5 | O75159 Q8IYZ4 | NM_014011 NM_144949 | |
| 4059 | SOCS7: (SOCS7 OR NAP4 OR SOCS6 OR CISH7) SUPPRESSOR OF CYTOKINE SIGNALING 7 (SOCS-7) | O14512 Q0IJ63 | NM_014598 | |
| 4078 | CISH: (CISH OR G18 OR CIS) CYTOKINE-INDUCIBLE SH2-CONTAINING PROTEIN (CIS) (CIS-1)(SOCS) (G18). | Q9Y5R1 Q9NSE2 Q9NS38 | NM_013324 NM_145071 | |
| 4085 | SOCS1: (SOCS1 OR SSI1 OR TIP3 OR JAB OR CISH1) SUPPRESSOR OF CYTOKINE SIGNALING 1 (SSI-1) | O15524 O15097 Q9NSA7 | NM_003745 | |
| 4087 | SOCS2: (SOCS2 OR CIS2 OR SSI2 OR STATI2) SUPPRESSOR OF CYTOKINE SIGNALING 2 (SOCS-2) | O14508 O14542 O95102 Q9UKS5 | NM_003877 | |
| 4089 | SOCS3: (SOCS3 OR CIS3 OR SSI3) SUPPRESSOR OF CYTOKINE SIGNALING 3 (SOCS-3) (CIS-3) | O14509 O14543 | NM_003955 | 1.20/10% |
| 4404 | EOMES: (EOMES OR TBR2) EOMESODERMIN HOMOLOG. | Q9UPM7 Q8TAZ2 O95936 | NM_005442 | |
| 4463 | CCL1: (CCL1 OR SCYA1) SMALL INDUCIBLE CYTOKINE A1 PRECURSOR (CCL1) (T LYMPHOCYTE-SECRETED PROTEIN I-309). | P22362 | NM_002981 | |
| 4467 | CCL2_HUMAN: (SCYA2 OR MCP1) SMALL INDUCIBLE CYTOKINE A2 PRECURSOR (MONOCYTE CHEMOTACTIC PROTEIN 1) (MCP-1) | P13500 Q9UDF3 | NM_002982 | |
| 4468 | CCL11: (SCYA11) EOTAXIN PRECURSOR (EOSINOPHIL CHEMOTACTIC PROTEIN). | P51671 P50877 Q92490 Q92491 | NM_002986 | |
| 4472 | CCL13_HUMAN: (CCL13 OR SCYA13 OR MCP4 OR NCC1) SMALL INDUCIBLE CYTOKINE A13 PRECURSOR (CCL13) | Q99616 O95689 | NM_005408 | |
| 4474 | CCL15-CCL14_1_HUMAN: (CCL15 OR SCYA15 OR MIP5 OR NCC3) SMALL INDUCIBLE CYTOKINE A15 PRECURSOR (CCL15) | Q16663 Q16627 Q13954 Q9UM74 | NM_004166 NM_004167 NM_032962 NM_032963 NM_032964 | |
| 4476 | CCL16_HUMAN: (CCL16 OR SCYA16 OR ILINCK OR NCC4) SMALL INDUCIBLE CYTOKINE A16 PRECURSOR (CCL16) | O15467 | NM_004590 | |
| 4478 | CCL17: (SCYA17 OR TARC OR A-152E5.3) SMALL INDUCIBLE CYTOKINE A17 | Q92583 Q2M287 | NM_002987 | |
| 4480 | CCL18_HUMAN: (CCL18 OR SCYA18 OR MIP4 OR PARC OR AMAC1 OR DCCK1) | P55774 Q53X71 | NM_002988 | |
| 4482 | CCL19: (SCYA19 OR MIP3B OR ELC) SMALL INDUCIBLE CYTOKINE A19 PRECURSOR (MIP-3-BETA) | Q99731 O00736 O00697 | NM_006274 | |
| 4487 | CCL20: (CCL20 OR SCYA20 OR MIP3A OR LARC) SMALL INDUCIBLE CYTOKINE A20 PRECURSOR (CCL20) | P78556 Q99664 Q53S51 | NM_004591 | |
| 4489 | CCL21: (SCYA21 OR SCYA21B OR SCYA21A) SMALL INDUCIBLE CYTOKINE A21 PRECURSOR(SLC). | O00585 | NM_002989 | |
| 4491 | CCL22: (CCL22 OR SCYA22 OR MDC OR A-152E5.1) SMALL INDUCIBLE CYTOKINE A22 PRECURSOR. | O00626 | NM_002990 | |
| 4494 | CCL23_HUMAN: (CCL23 OR SCYA23 OR MIP3 OR MPIF1) SMALL INDUCIBLE CYTOKINE A23 PRECURSOR (CCL23) | P55773 O00174 O75950 Q52LD4 | NM_005064 NM_145898 | |
| 4496 | CCL24: (CCL24 OR SCYA24 OR MPIF2) SMALL INDUCIBLE CYTOKINE A24 PRECURSOR (CCL24) (MPIF-2) (CK-BETA-6) | O00175 | NM_002991 | |
| 4500 | CCL26_HUMAN: (CCL26 OR SCYA26) SMALL INDUCIBLE CYTOKINE A26 PRECURSOR (CCL26)(CC CHEMOKINE IMAC). | Q9Y258 Q52LV8 | NM_006072 | |
| 4502 | CCL27: (SCYA27 OR ILC) SMALL INDUCIBLE CYTOKINE A27 PRECURSOR (CC CHEMOKINE ILC) | Q9Y4X3 | NM_006664 | |
| 4504 | CCL3-CCL3L1-CCL3L3_HUMAN: ((CCL3 OR SCYA3 OR G0S19-1 OR MIP1A) AND (CCL3L1 OR SCYA3L1 OR G0S19-2)) | P10147 Q53YA5 Q96I68 P16619 | NM_001001437 NM_002983 NM_021006 | 0.67/23% |
| 4508 | CCL4: (SCYA4 OR MIP1B OR LAG1) SMALL INDUCIBLE CYTOKINE A4 PRECURSOR (MIP-1-BETA) (PAT 744) (H400) (SIS-GAMMA). | P13236 P22617 Q13704 Q3SXL8 Q6FGI8 | NM_002984 | |
| 4510 | CCL5: (SCYA5) SMALL INDUCIBLE CYTOKINE A5 PRECURSOR (SIS-DELTA) (T CELL-SPECIFIC PROTEIN P228) (TCP228). | P13501 O43646 Q4ZGJ1 Q9NYA2 | NM_002985 | |
| 4514 | CCL7: (SCYA7 OR MCP3) SMALL INDUCIBLE CYTOKINE A7 PRECURSOR (MCP-3) (NC28) | P80098 | NM_006273 | |
| 4516 | CCL8_HUMAN: (SCYA8 OR SCYA10 OR MCP2) SMALL INDUCIBLE CYTOKINE A8 PRECURSOR (HC14) | P80075 P78388 | NM_005623 | |
| 4522 | CX3CL1: (SCYD1 OR FKN OR NTT OR A-152E5.2) FRACTALKINE PRECURSOR(SMALL INDUCIBLE CYTOKINE D1). | P78423 O00672 | NM_002996 | |
| 4524 | CXCL10: (SCYB10 OR INP10 OR MOB1 OR CRG-2 OR IFI10) SMALL INDUCIBLE (C7). | P02778 Q96QJ5 | NM_001565 | |
| 4526 | CXCL11: (SCYB11 OR SCYB9B OR ITAC) SMALL INDUCIBLE CYTOKINE B11 PRECURSOR (BETA-R1) (CXCL11). | O14625 Q92840 | NM_005409 | |
| 4528 | CXCL12: (CXCL12 OR SDF1) STROMAL CELL-DERIVED FACTOR 1 PRECURSOR (SDF-1) | P48061 | NM_000609 | |
| 4530 | CXCL13: (BLC OR BCA1) B LYMPHOCYTE CHEMOATTRACTANT PRECURSOR(BCA-1) (ANGIE). | O43927 | NM_006419 | |
| 4532 | CXCL14: (SCYB14 OR NJAC) SMALL INDUCIBLE CYTOKINE B14 PRECURSOR (KIDNEY-EXPRESSED CHEMOKINE CXC). | O95715 Q6UW97 Q9BTR1 Q86U69 | NM_004887 | |

TABLE 1-continued

| Gene# | Name | UniProt/tremble | RefSeq accession no. | Change value |
|---|---|---|---|---|
| 4543 | CXCL6_HUMAN: (CXCL6 OR SCYB6 OR GCP2) SMALL INDUCIBLE CYTOKINE B6 PRECURSOR (CXCL6) | P80162 Q4W5D4 | NM_002993 | |
| 4545 | CXCL7: (SCYB7 OR PPBP OR CTAP3 OR TGB1 OR THBGB1) PLATELET BASIC PROTEIN PRECURSOR (PBP) | P02775 Q6IBJ8 | NM_002704 | |
| 4547 | CXCL9: (CXCL9 OR MIG OR SCYB9) SMALL INDUCIBLE CYTOKINE B9 PRECURSOR (CXCL9) (MIG) | Q07325 Q503B4 | NM_002416 | |
| 4549 | GITRL: (TNFSF18 OR AITRL OR GITRL OR TL6) TUMOR NECROSIS FACTOR LIGAND SUPERFAMILY MEMBER 18 (AITRL). | O95852 Q9UNG2 | NM_005092 | |
| 4551 | XCL1-XCL2_HUMAN: ((XCL1 OR SCYC1 OR LTN) AND (XCL2 OR SCYC2)) | P47992 Q52MA8 Q9UBD3 | NM_002995 NM_003175 | 0.01/3% |
| 4707 | CSF2: (CSF2 OR GMCSF OR CSFGM) GRANULOCYTE-MACROPHAGE COLONY-STIMULATING FACTOR PRECURSOR (GM-CSF) | P04141 Q8NFI6 | NM_000758 | |
| 4716 | IFNA2_HUMAN: (IFNA2) INTERFERON ALPHA-2 PRECURSOR (INTERFERON ALPHA-A) (LEIF A). | P01563 Q96KI6 P01564 Q14606 | NM_000605 | |
| 4720 | IFNAR1: (IFNAR1 OR IFNAR OR IFAR) INTERFERON-ALPHA/BETA RECEPTOR ALPHA CHAIN PRECURSOR (CD118). | P17181 Q53GW9 Q53H11 Q8WTZ2 | NM_000629 | |
| 4722 | IFNAR2: (IFNAR2 OR IFNARB) INTERFERON-ALPHA/BETA RECEPTOR BETA CHAIN PRECURSOR (IFN-R) | P48551 | NM_000874 | |
| 4727 | IGF1R: (IGF1R) INSULIN-LIKE GROWTH FACTOR I RECEPTOR PRECURSOR(CD221 ANTIGEN). | P08069 | NM_000875 | |
| 4729 | IL10RA: (IL10RA OR IL10R) INTERLEUKIN-10 RECEPTOR ALPHA CHAIN PRECURSOR (IL-10R-A) (IL-10R1) (CDW210A ANTIGEN). | Q13651 | NM_001558 | 1.18/25% |
| 4736 | LIF: (LIF OR HILDA) LEUKEMIA INHIBITORY FACTOR PRECURSOR (LIF) (DIFFERENTIATION- STIMULATING FACTOR) | P15018 Q52LZ2 | NM_002309 | |
| 4739 | LIFR: (LIFR) LEUKEMIA INHIBITORY FACTOR RECEPTOR PRECURSOR (LIF-R) (CD118 ANTIGEN) (LIFRA). | P42702 Q6LCD9 | NM_002310 | |
| 4747 | IGF2R: (IGF2R OR MPRI) CATION-INDEPENDENT MANNOSE-6-PHOSPHATE RECEPTOR PRECURSOR (M6P/IGF2R) | P11717 Q7Z7G9 Q96PT5 | NM_000876 | |
| 4754 | OSM: (OSM) ONCOSTATIN M PRECURSOR (OSM). | P13725 | NM_020530 | 0.33/—% |
| 4757 | OSMR: (OSMR OR OSMRB) ONCOSTATIN-M SPECIFIC RECEPTOR SUBUNIT BETA PRECURSOR. | Q99650 Q6P4E8 Q96QJ6 | NM_003999 | |
| 4775 | TGFBR1: (TGFBR1) TGF-BETA RECEPTOR TYPE I PRECURSOR (SKR4) (ACTIVIN RECEPTOR-LIKE KINASE 5) (ALK-5). | P36897 | NM_004612 | |
| 4777 | TGFBR2: (TGFBR2) TGF-BETA RECEPTOR TYPE II PRECURSOR (EC 2.7.1.37) (TGFR-2) (TGF-BETA TYPE II RECEPTOR). | P37173 Q99474 Q15580 Q6DKT6 | NM_001024847 NM_003242 | |
| 4847 | IL1RL2: (IL1RL2 OR IL1RRP2) INTERLEUKIN 1 RECEPTOR-LIKE 2 PRECURSOR (IL-1RRP2) (IL1R-RP2). | Q9HB29 Q45H74 Q13525 | NM_003854 | |
| 4849 | IL18R1: (IL1RRP OR IL18R1) INTERLEUKIN 18 RECEPTOR 1 PRECURSOR (IL-1RRP) (CD218A ANTIGEN) (CDW218A). | Q13478 | NM_003855 | |
| 4978 | CNTF-ZFP91_1: (CNTF) CILIARY NEUROTROPHIC FACTOR (ZFP91) (ZINC FINGER PROTEIN ZFP91) (PZF) | P26441 Q86V47 Q96JP5 Q96QA3 Q96JP4 | NM_000614 NM_170768 | |
| 4980 | CSF3: (CSF3) GRANULOCYTE COLONY-STIMULATING FACTOR PRECURSOR (G-CSF) (PLURIPOIETIN) (FILGRASTIM) (LENOGRASTIM). | P09919 | NM_000759 NM_172219 NM_172220 | |
| 5056 | IGF1_1: (IGF1 OR IBP1) INSULIN-LIKE GROWTH FACTOR IA PRECURSOR (IGF-IA) (SOMATOMEDIN C)(IGF-IB). | Q14620 P01343 P05019 | NM_000618 | |
| 5211 | IGF2_1: (IGF2) INSULIN-LIKE GROWTH FACTOR II PRECURSOR (IGF-II) (SOMATOMEDIN A). | P01344 Q1WM26 Q9UC68 P78449 Q14299 Q9UC69 | NM_000612 NM_001007139 NM_001042377 | 0.79/1% |
| 5213 | LEPR: (OBR OR LEPR OR DB OR FA) LEPTIN RECEPTOR PRECURSOR (LEP-R)(HUB219) (B219) (CD295 ANTIGEN). | P48357 Q92919 Q92920 Q92921 Q13592 Q13593 Q13594 | NM_002303 | |
| 5219 | NGFB: (NGFB) BETA-NERVE GROWTH FACTOR PRECURSOR (BETA-NGF). | P01138 Q6FHA0 Q9P2Q8 Q96P60 Q9UKL8 | NM_002506 | |
| 5544 | OB_2: (LEP OR OB) LEPTIN PRECURSOR (OBESITY FACTOR) (OBESE PROTEIN). | P41159 O15158 Q56A88 | NM_000230 | |
| 9231 | EPOR: (EPOR) ERYTHROPOIETIN RECEPTOR PRECURSOR (EPO-R). | Q15443 P19235 | NM_000121 | |
| 9707 | NRP1: (NRP1 OR NRP OR VEGF165R) NEUROPILIN-1 PRECURSOR(CD304 ANTIGEN). | Q96IH5 O60461 O14786 | NM_003873 | |
| 11163 | IFNB1: (IFNB1 OR IFNB OR IFB) INTERFERON BETA PRECURSOR (IFN-BETA) (FIBROBLAST INTERFERON). | P01574 | NM_002176 | |
| 11325 | ST16: (IL24 OR ST16 OR MDA7) SUPPRESSION OF TUMORIGENICITY 16 PROTEIN PRECURSOR (MDA-7) (MOB-5) (C49A). | Q96DB0 Q96KG4 Q13007 | NM_006850 NM_181339 | |
| 11343 | ZMDA1: (IL19 OR ZMDA1) INTERLEUKIN-19 PRECURSOR (IL-19)(NG.1). | Q96QR4 Q9NUA0 Q9UHD0 | NM_013371 NM_153758 | |
| 11750 | CXCL16: (0910001K24RIK) SR-PSOX (TRANSMEMBRANE CHEMOKINE CXCL16) (0910001K24RIK PROTEIN). | Q9H2A7 Q8TC80 Q96K63 Q9BXD6 Q9H2F6 | NM_022059 | 5.42/65% |
| 11755 | TNFRSF21: (TNFRSF21 OR DR6) (TNFR-RELATED DEATH RECEPTOR 6) (DEATH RECEPTOR 6) (DJ18U13.1). | O75509 Q96D86 | NM_014452 | 0.16/1% |
| 11779 | FLT3LG: (FLT3LG) SL CYTOKINE PRECURSOR (FMS-RELATED TYROSINE KINASE 3 LIGAND) (FLT3 LIGAND). | P49771 | NM_001459 | 1.07/3% |

TABLE 1-continued

| Gene# | Name | UniProt/tremble | RefSeq accession no. | Change value |
|---|---|---|---|---|
| 11794 | GATA1: (GATA1 OR GF1 OR ERYF1) ERYTHROID TRANSCRIPTION FACTOR (GATA-1) (ERYF1) (GF-1) (NF-E1). | P15976 Q96GB8 | NM_002049 | |
| 11797 | GATA2: (GATA2) ENDOTHELIAL TRANSCRIPTION FACTOR GATA-2. | P23769 Q9BUJ6 | NM_032638 | |
| 11800 | GATA3: (GATA3) TRANS-ACTING T-CELL SPECIFIC TRANSCRIPTION FACTOR GATA-3. | P23771 Q96J16 | NM_002051 | |
| 11804 | GATA4: (GATA4) TRANSCRIPTION FACTOR GATA-4 (GATA BINDING FACTOR-4). | P43694 | NM_002052 | |
| 11819 | GZMB: (GZMB OR CTLA1 OR CTLA-1 OR GRB OR CSPB OR CGL1) GRANZYME B(G, H) PRECURSOR | P10144 Q8N1D2 | NM_004131 | |
| 11824 | HAVCR1: (HAVCR1 OR TIM1 OR TIMD1) HEPATITIS A VIRUS CELLULAR RECEPTOR 1 PRECURSOR (TIM-1) (TIM) (HHAVCR-1). | O43656 Q96D42 | NM_012206 | |
| 11836 | IL22_HUMAN: (IL22 OR IL-22 OR IL22A OR ILTIFA OR ILTIF) INTERLEUKIN-22 PRECURSOR (INTERLEUKIN 22) (IL-22A). | Q9GZX6 | NM_020525 | |
| 11839 | IL10RB: (IL10RB OR CRFB4) INTERLEUKIN-10 RECEPTOR BETA CHAIN PRECURSOR (IL-10R-B) (CDW210B ANTIGEN). | Q08334 Q9BUU4 | NM_000628 | |
| 11842 | IL12RB1_1: (IL12RB1 OR IL12RB OR IL12R) IL-12 RECEPTOR BETA-1 CHAIN PRECURSOR (IL-12R-BETA1) (CD212 ANTIGEN). | P42701 | NM_005535 | |
| 11845 | IL12RB2: (IL12RB2) INTERLEUKIN-12 RECEPTOR BETA-2 CHAIN PRECURSOR (IL-12 RECEPTOR BETA-2) (IL-12R-BETA2). | Q99665 | NM_001559 | |
| 11854 | IL17RA: (IL17RA OR IL17R) INTERLEUKIN-17 RECEPTOR A PRECURSOR (IL-17 RECEPTOR) (CD217 ANTIGEN) (CDW217). | O43844 Q96F46 | NM_014339 | |
| 11857 | IL1RL1_1: (IL1RL1 OR ST2 OR STE2 OR LY84 OR DER4 OR T1) (FIT-1) (MGC32623) (FIT-1S) (FIT-1M). | Q01638 Q53TU7 Q9UQ44 Q9ULV7 Q8NEJ3 | NM_003856 NM_016232 | |
| 11860 | IL21: (IL21) INTERLEUKIN 21. | Q9HBE4 | NM_021803 | |
| 12040 | PRLR: (PRLR) PROLACTIN RECEPTOR PRECURSOR (PRL-R). | P16471 Q16354 Q9BX87 | NM_000949 | |
| 12076 | SCYA28: (SCYA28) SMALL INDUCIBLE CYTOKINE A28 PRECURSOR (CCL28)(MEC). | Q9NRJ3 | NM_019846 NM_148672 | |
| 12124 | TNFRSF13B: (TNFRSF13B OR TACI) TUMOR NECROSIS FACTOR RECEPTOR SUPERFAMILY MEMBER 13B (CD267 ANTIGEN). | O14836 Q7Z6F5 | NM_012452 | |
| 12163 | ZCYTO7: (IL17B OR ZCYTO7 OR NIRF OR IL20) INTERLEUKIN-17B PRECURSOR (IL-17B) (INTERLEUKIN-20). | Q9UHF5 | NM_014443 | |
| 12329 | IGF1_2: (IGF1 OR IBP1) INSULIN-LIKE GROWTH FACTOR IB PRECURSOR (IGF-IB) (SOMATOMEDIN C). | P05019 | — | |
| 12797 | PRL_2: (PRL) PROLACTIN PRECURSOR (PRL). | P01236 Q92996 Q15199 | NM_000948 | |
| 13073 | IFRD1: (IFRD1) INTERFERON-RELATED DEVELOPMENTAL REGULATOR 1 (NERVE GROWTH FACTOR-INDUCIBLE PROTEIN PC4). | O75234 Q5U013 Q9BVE4 O00458 | NM_001550 | |
| 14752 | VGR1: (FLT1 OR FLT OR FRT) VASCULAR ENDOTHELIAL GROWTH FACTOR RECEPTOR 1 PRECURSOR(VEGFR-1)(FLT-1) | P16057 O60722 P17948 Q12954 | NM_002019 | |
| 17086 | CMTM6: (CMTM6 OR CKLFSF6) CKLF-LIKE MARVEL TRANSMEMBRANE DOMAIN-CONTAINING PROTEIN 6(FLJ20396). | Q9NX76 | NM_017801 | |
| 17164 | IL22R: (IL22R) IL-22 RECEPTOR. | Q9HB22 | NM_021258 | 0.49/26% |
| 17831 | CSF1: (CSF1 OR CSFM) MACROPHAGE COLONY STIMULATING FACTOR-1 PRECURSOR (CSF-1) (MCSF). | P09603 Q14806 Q13130 Q14086 Q9UQR8 | NM_000757 NM_172210 NM_172211 NM_172212 | |
| 17935 | IFNGR2: (IFNGR2 OR IFNGT1) INTERFERON-GAMMA RECEPTOR BETA CHAIN PRECURSOR (INTERFERON-GAMMA TRANSDUCER-1). | P38484 Q9BTL5 | NM_005534 | |
| 18152 | GHR: (GHR) HIGH MOLECULAR WEIGHT GROWTH HORMONE RECEPTOR/BINDING PROTEIN PRECURSOR. | P10912 Q9HCX2 | NM_000163 | |
| 18202 | IFI-78K_HUMAN: (MX1) INTERFERON-INDUCED GTP-BINDING PROTEIN MX1 (IFI-78K). | P20591 | NM_002462 | |
| 19768 | GZMH_HUMAN: (GZMH OR CTSGL2 OR CGL2) GRANZYME H PRECURSOR (CTSGL2) (CCP-X) (CSP-C). | P20718 | NM_033423 | |
| 20039 | GATA6: (GATA6) TRANSCRIPTION FACTOR GATA-6 (GATA BINDING FACTOR-6)(DNA BINDINGPROTEIN GATA-GT2). | Q92908 P78327 | NM_005257 | |
| 20042 | GZMA: (GZMA OR CTLA3 OR HFSP) GRANZYME A PRECURSOR(FRAGMENTIN 1) (TSP-1) (MTSP-1). | P12544 | NM_006144 | |
| 20045 | GZMK: (GZMK OR TRYP2) GRANZYME K PRECURSOR(GRANZYME 3) (NK-TRYPTASE-2) (NK-TRYP-2) (FRAGMENTIN 3). | P49863 | NM_002104 | |
| 20048 | GZMM: (GZMM OR MET1) GRANZYME M PRECURSOR (EC 3.4.21.—) (MET-ASE). | P51124 | NM_005317 | |
| 20568 | SEMB: (SEMA4A OR SEMAB OR SEMB) SEMAPHORIN 4A PRECURSOR (SEMAPHORIN B) (SEMA B). | Q8WUA9 Q9H3S1 | NM_022367 | |
| 21165 | IL13RA1: (IL13RA1 OR IL13RA OR IL13R) INTERLEUKIN-13 RECEPTOR ALPHA-1 CHAIN PRECURSOR (CD213A1 ANTIGEN). | P78552 Q99656 O95646 | NM_001560 | |
| 22278 | EDAR: (EDAR) ECTODYSPLASIN-A RECEPTOR PROTEIN. | Q9UND9 Q9UNE0 | NM_022336 | 0.03/—% |
| 22287 | KDR_1: (KDR) DEATH RECEPTOR CANDIDATE (FLJ22573) (MGC30332). | Q9H665 | NM_024660 | |
| 22822 | SCYE1: (SCYE1 OR EMAP2) MULTISYNTHETASE COMPLEX AUXILIARY COMPONENT P43. | Q6FG28 Q96CQ9 Q12904 | NM_004757 | |

TABLE 1-continued

| Gene# | Name | UniProt/tremble | RefSeq accession no. | Change value |
|---|---|---|---|---|
| 23301 | TNFRSF13C: (TNFRSF13C OR BAFFR OR) TUMOR NECROSIS FACTOR RECEPTOR SUPERFAMILY MEMBER 13C(CD268 ANTIGEN). | Q96RJ3 | NM_052945 | |
| 23439 | KDR_2: (KDR) DEATH RECEPTOR CANDIDATE (FLJ22573) (MGC30332). | Q9H665 | NM_024660 | |
| 23442 | KDR_3: (KDR) DEATH RECEPTOR CANDIDATE (FLJ22573) (MGC30332). | Q9H665 | NM_024660 | |
| 23485 | TNFRSF19L: (TNFRSF19L OR RELT) TUMOR NECROSIS FACTOR RECEPTOR SUPERFAMILY MEMBER 19L PRECURSOR | Q86V34 Q96JU1 Q9BUX7 Q969Z4 | NM_032871 NM_152222 | 0.22/—% |
| 23488 | TNFRSF12A: (TNFRSF12A OR FN14) (TWEAKR) (CD266 ANTIGEN). | Q9HCS0 Q9NP84 | NM_016639 | |
| 23491 | VEGI: (TNFSF15 OR VEGI OR TL1) TUMOR NECROSIS FACTOR LIGAND SUPERFAMILY MEMBER 15. | O95150 | NM_005118 | |
| 23494 | EDA2R: (EDA2R OR TNFRSF27 OR XEDAR) (UNQ2448/PRO34080/PRO5727). | Q6UWM2 Q8IZA6 Q9HAV5 | NM_021783 | |
| 25052 | KITLG: (KITLG OR MGF OR SCF) KIT LIGAND PRECURSOR (C-KIT LIGAND) (STEM CELL FACTOR) (SCF)(MGF). | Q16487 Q9UQK7 P21583 | NM_003994 | |
| 25954 | IL13RA2: (IL13RA2 OR IL13R) INTERLEUKIN-13 RECEPTOR ALPHA-2 CHAIN PRECURSOR (CD213A2 ANTIGEN). | Q14627 O00667 | NM_000640 | |
| 26325 | CCBP2: (CCBP2 OR CMBRK9 OR CCR10) CHEMOKINE BINDING PROTEIN 2 (CC-CHEMOKINE RECEPTOR CCR10). | O00590 O00537 Q96A02 Q86UN9 | NM_001296 | |
| 26328 | CCR11: (CCR11 OR CCBP2 OR VSHK1) C-C CHEMOKINE RECEPTOR TYPE 11 (C-C CKR-11)(GPCR14). | Q9NPB9 | NM_016557 NM_178445 | |
| 26443 | GPR44: (GPR44 OR CRTH2 OR DL1R) PUTATIVE G PROTEIN-COUPLED RECEPTOR GPR44 (CD294 ANTIGEN). | Q4QRI6 Q9Y5Y4 O94765 | NM_004778 | |
| 26473 | IL17F: (IL17F OR IL24) INTERLEUKIN-17F PRECURSOR (IL-17F) (INTERLEUKIN-24) (CYTOKINE ML-1). | Q96PD4 Q9NUE6 Q96PI8 Q7Z6P4 | NM_052872 NM_172343 | |
| 26479 | IL1RN: (IL1RN OR IL1RA) INTERLEUKIN-1 RECEPTOR ANTAGONIST PROTEIN PRECURSOR (IL-1RA) (ICIL-1RA) (IRAP) (IL-1RN). | P18510 Q96GD6 Q14628 Q9UPC0 Q7RTZ4 | NM_000577 NM_173841 NM_173842 NM_173843 | |
| 26482 | IL20: (IL20 OR ZCYTO10) INTERLEUKIN-20 PRECURSOR (IL-20) (UNQ852/PRO1801). | Q9NYY1 Q96QZ6 | NM_018724 | |
| 26485 | IL21R: (IL21R OR NILR) INTERLEUKIN 21 RECEPTOR PRECURSOR (IL-21R) (NOVEL INTERLEUKIN RECEPTOR) | Q9HBE5 Q9HB91 Q96HZ1 | NM_021798 NM_181078 NM_181079 | |
| 26660 | TGFBR3: (TGFBR3) TGF-BETA RECEPTOR TYPE III PRECURSOR (TGFR-3) (BETAGLYCAN). | Q03167 Q5T2T4 Q5U731 Q9UGI2 | NM_003243 | |
| 26828 | IFNA10-IFNA17-IFNA4-IFNA16-IFNA7-IFNA14_HUMAN: (IFNA10) INTERFERON ALPHA-10 PRECURSOR(IFNA4) | P01566 P01571 P05014 P05015 P01567 P01570 Q14639 P13358 Q14607 | NM_002171 NM_002172 NM_002173 NM_021057 NM_021068 NM_021268 | |
| 26829 | IFNA1-IFNA13_HUMAN: (IFNA1 AND IFNA13) INTERFERON ALPHA-1/13 PRECURSOR (INTERFERON ALPHA-D) (LEIF D). | Q14605 Q9UMJ3 Q5VYQ2 P01562 | NM_006900 NM_024013 | |
| 26830 | IFNA21_HUMAN: (IFNA21) INTERFERON ALPHA-21 PRECURSOR (INTERFERON ALPHA-F) (LEIF F). | P01568 | NM_002175 | 5.34/—% |
| 26832 | IFNA6_HUMAN: (IFNA6) INTERFERON ALPHA-6 PRECURSOR (INTERFERON ALPHA-K) (LEIF K) (INTERFERON ALPHA-54). | P05013 | NM_021002 | |
| 26833 | IFNA8_HUMAN: (IFNA8) INTERFERON ALPHA-8 PRECURSOR (INTERFERON ALPHA-B2) (INTERFERON ALPHA-B) (LEIF B). | P32881 P09236 P01565 | NM_002170 | |
| 26840 | IFNW1_HUMAN: (IFNW1) INTERFERON OMEGA-1 PRECURSOR (INTERFERON ALPHA-II-1). | P05000 | NM_002177 | |
| 27246 | PTN: (PTN OR NEGF1 OR HBNF1) PLEIOTROPHIN PRECURSOR (PTN)(OSF-1) | P21246 | NM_002825 | |
| 28535 | IL17D: (IL27) INTERLEUKIN 27 PRECURSOR (IL-17D) (IL27A) (IL17D) | Q8TAD2 | NM_138284 | |
| 29471 | TNFRSF10C_HUMAN: (TNFRSF10C OR DCR1 OR TRAILR3 OR TRID OR LIT) (DCR1) (DECOY TRAIL RECEPTOR WITHOUT DEATH DOMAIN) | Q6UXM5 O14798 O14755 | NM_003841 | |
| 30254 | CKLFSF1_HUMAN: (CKLFSF1) CHEMOKINE-LIKE FACTOR SUPER FAMILY 1. | Q8IZ96 Q96JC2 Q8IZ94 Q8IZ93 Q8IZ95 Q8IU76 Q8IU83 Q8IU86 Q8IU93 Q | NM_052999 NM_181268 NM_181269 NM_181270 NM_181271 NM_181272 NM_1 | 1.44/—% |
| 30399 | WSX1: (WSX1 OR CRL1 OR TCCR) CLASS I CYTOKINE RECEPTOR (CRL1 PROTEIN) (IL-27R-ALPHA) (WSX-1). | Q6UWB1 O60624 | NM_004843 | |
| 30402 | CCR2_1: (CCR2 OR CMKBR2) C-C CHEMOKINE RECEPTOR TYPE 2 (C-C CKR-2) | P41597 | NM_000647 | |
| 30405 | CCR2_2: (CCR2 OR CMKBR2) C-C CHEMOKINE RECEPTOR TYPE 2 (C-C CKR-2)(CCR2B). | P41597 | NM_000648 | |
| 30408 | CCR5: (CCR5 OR CMKBR5) C-C CHEMOKINE RECEPTOR TYPE 5 (C-C CKR-5)(CD195 ANTIGEN). | P51681 O14692 O14693 O14695 O14696 O14697 O14698 O14699 O14700 O | NM_000579 | |

TABLE 1-continued

| Gene# | Name | UniProt/tremble | RefSeq accession no. | Change value |
|---|---|---|---|---|
| 30430 | IL8RA: (IL8RA OR CXCR1) HIGH AFFINITY INTERLEUKIN-8 RECEPTOR A (IL-8R A)(CXCR-1)(CDW128A). | Q2YEF8 Q2YEG4 Q2YEG5 Q2YEG7 Q2YEG8 Q53R18 Q6IN95 Q8N6T6 P25024 Q | NM_000634 | 1.12/—% |
| 30431 | IL8RB: (IL8RB OR CXCR2) HIGH AFFINITY INTERLEUKIN-8 RECEPTOR B (IL-8R B) (CXCR-2) | P25025 Q9P2T6 Q9P2T7 Q8IUZ1 | NM_001557 | 0.07/—% |
| 30456 | IL15RA: (IL15RA) INTERLEUKIN-15 RECEPTOR ALPHA CHAIN PRECURSOR. | Q6B0J2 Q7LDR4 Q7Z609 Q13261 | NM_002189 NM_172200 | |
| 30459 | PF4-PF4V1_HUMAN: (SCYB4 OR PF4) PLATELET FACTOR 4 PRECURSOR (PF-4) (CXCL4). | P02776 P10720 | NM_002619 NM_002620 | |
| 30503 | MPL: (MPL OR TPOR) THROMBOPOIETIN RECEPTOR PRECURSOR (CD110 ANTIGEN). | P40238 | NM_005373 | |
| 30523 | CLF-1: (CLF-1) CYTOKINE-LIKE FACTOR-1 PRECURSOR. | O75462 Q9UHH5 | NM_004750 | 4.67/76% |
| 30526 | CRAM: (CRAM-A OR CRAM-B OR CCRL2 OR CMKBR1L2 OR L-CCR OR E01 OR 1810047I05RIK). | Q4VBBO Q6IPX0 O75307 Q9UPG0 O00421 Q96KP5 | NM_003965 | |
| 30529 | CRF2-S1: (CRF2-S1 OR IL22BP OR IL22RA2 OR IL-22BP) SOLUBLE CYTOKINE CLASS II RECEPTOR | Q6UWM1 Q96A41 Q969J5 Q96QR0 | NM_052962 NM_181309 NM_181310 | |
| 30532 | CRL2: (CRL2 OR IL-XR OR CRLM2) CYTOKINE RECEPTOR CRL2 PRECURSOR (IL-XR) | Q9HC73 Q9H5R3 | NM_022148 | |
| 30535 | IL31RA: (IL31RA OR CRL3) INTERLEUKIN 31RA (INTERLEUKIN-31 RECEPTOR ALPHA CHAIN PRECURSOR) (CRL3 PROTEIN) | Q6EBC4 Q6EBC6 Q6EBC3 Q6UWL8 Q6EBC5 Q8NI17 Q8WYJ0 | NM_139017 | |
| 30538 | EBI3: (EBI3) CYTOKINE RECEPTOR PRECURSOR (EPSTEIN-BARR VIRUS INDUCED GENE 3) (IL27) (IL-27) | Q14213 O75269 | NM_005755 | |
| 30566 | IL20RB: (IL20RB) IL20RB INTERLEUKIN 20 RECEPTOR BETA (IL10R-LIKE). | Q8IYY5 Q8TAJ7 Q6UXL0 Q6P438 | NM_144717 | |
| 30570 | IL11RA: (IL11RA1 OR IL11RA OR ETL2 OR ET12/IL11 REC) INTERLEUKIN-11 RECEPTOR ALPHA CHAIN 1 PRECURSOR (NR1) | Q16542 Q14626 Q7KYJ7 | NM_004512 NM_147162 | |
| 30572 | IL1F10: (IL1F10 OR FIL1T OR IL1HY2 OR FKSG75) INTERLEUKIN 1 FAMILY MEMBER 10 (IL-1F10) | Q7RTZ5 Q56AT8 Q8WWZ1 Q969H5 Q9BYX1 | NM_032556 NM_173161 | |
| 30575 | IL1F5: (IL1F5 OR FIL1D OR IL1HY1 OR IL1L1 OR IL1RP3) INTERLEUKIN 1 FAMILY MEMBER 5 (IL-1F5) | Q7RTZ6 Q56AT9 Q9UBH0 | NM_012275 NM_173170 | 1.15/57% |
| 30578 | IL1F6: (IL1F6 OR IL1E OR FIL1E) INTERLEUKIN 1 FAMILY MEMBER 6 (IL-1F6). | Q7RTZ8 Q5BLR4 Q9UHA7 | NM_014440 | |
| 30581 | IL1F7_HUMAN: (IL1F7 OR FIL1Z OR IL1H4 OR IL1RP1) INTERLEUKIN 1 FAMILY MEMBER 7 PRECURSOR. | Q56AP9 Q9NZH6 Q8TD04 Q8TD05 Q9HBF2 Q9HBF3 Q9UHA6 | NM_014439 NM_173202 NM_173203 NM_173204 NM_173205 | |
| 30582 | IL1F8: (IL1F8 OR IL1H2) INTERLEUKIN 1 FAMILY MEMBER 8 (IL-1F8) (IL-1H2). | Q53SR6 Q9NZH7 Q9UHA5 Q7RTZ7 | NM_014438 NM_173178 | |
| 30585 | IL1F9: (IL1F9 OR IL1H1 OR IL1E OR IL1RP2) INTERLEUKIN 1 FAMILY MEMBER 9 (IL-1F9)(IL-1RP2). | Q6UVX7 Q7RTZ9 Q56B91 Q9NZH8 | NM_019618 | |
| 30588 | IL20RA: (IL20RA OR ZCYTOR7) INTERLEUKIN-20 RECEPTOR ALPHA CHAIN PRECURSOR (IL-20R-ALPHA) (IL-20R1). | Q9UHF4 Q96SH8 Q96SH7 Q6UWA9 | NM_014432 | 0.64/—% |
| 30591 | IL23A: (IL23A) INTERLEUKIN 23 P19 SUBUNIT (INTERLEUKIN 23, ALPHA SUBUNIT P19) (SGRF) (SGRF PRECURSOR) | Q6NZ80 Q6NZ82 Q9H2A5 Q9NPF7 | NM_016584 | |
| 30595 | IL23R: (IL23R OR IL-23R) INTERLEUKIN-23 RECEPTOR. | Q4VGP1 Q4VGP2 Q4VGP3 Q4VGP4 Q4VGP5 Q4VGP6 Q5VWK5 Q5VWK7 Q8NFQ9 Q | NM_144701 | |
| 30601 | IL28RA: (IL28RA OR CRF2/12 OR LICR2) (PUTATIVE CLASS II CYTOKINE RECEPTOR CRF2/12). | Q8IZI8 Q8IU57 Q8IV66 Q8IZI7 Q6ZML8 | NM_170743 NM_173064 NM_173065 | |
| 30621 | THPO: (THPO) THROMBOPOIETIN PRECURSOR (MEGAKARYOCYTE COLONY STIMULATING FACTOR)(MGDF). | P40225 Q13020 Q15790 Q15791 Q15792 | NM_000460 NM_199228 NM_199356 | 0.63/20% |
| 30654 | IL17C: (IL17C) INTERLEUKIN-17C PRECURSOR (IL-17C) (CYTOKINE CX2). | Q3MIG8 Q9P0M4 Q9HC75 | NM_013278 | 1.09/7% |
| 30672 | TNFRSF18: (TNFRSF18 OR GITR OR AITR) TUMOR NECROSIS FACTOR RECEPTOR SUPERFAMILY MEMBER 18 PRECURSOR. | Q9Y5U5 O95851 Q9NYJ9 | NM_004195 NM_148901 NM_148902 | |
| 30673 | TNFRSF4: (TNFRSF4 OR TXGP1L OR OX40 OR TXGP1) (CD134 ANTIGEN) (MRC OX40) (OX40L RECEPTOR) | Q5T7M0 P43489 Q13663 | NM_003327 | |
| 30779 | SOCS4: (SOCS4 OR SOCS7) SUPPRESSOR OF CYTOKINE SIGNALING 4 (SUPPRESSOR OF CYTOKINE SIGNALING 7) (SOCS-7). | Q8WXH5 | NM_080867 NM_199421 | |
| 30806 | TNFRSF17: (TNFRSF17 OR BCMA OR BCM) TUMOR NECROSIS FACTOR RECEPTOR SUPERFAMILY MEMBER 17(CD269 ANTIGEN). | Q02223 | NM_001192 | |
| 30807 | BLR1: (BLR1 OR CXCR5 OR GPCR6 OR MDR15) C-X-C CHEMOKINE RECEPTOR TYPE 5 (CXC-R5)(CD185 ANTIGEN). | P32302 Q14811 | NM_001716 NM_032966 | |
| 30808 | CNTFR: (CNTFR) CILIARY NEUROTROPHIC FACTOR RECEPTOR ALPHA PRECURSOR (CNTFR ALPHA). | P26992 | NM_001842 NM_147164 | 0.99/7% |
| 30809 | EDA_2: (ED1 OR EDA OR TA) ECTODYSPLASIN A (ECTODERMAL DYSPLASIA PROTEIN). | Q5JUM7 Q92838 O75910 Q9UP77 Q9Y6L0 Q9Y6L1 Q9Y6L2 Q9Y6L3 Q9Y6L4 | NM_001005609 NM_001399 | |

TABLE 1-continued

| Gene# | Name | UniProt/tremble | RefSeq accession no. | Change value |
|---|---|---|---|---|
| 30815 | GATA5: (GATA5) TRANSCRIPTION FACTOR GATA-5 (GATA BINDING FACTOR-5). | Q9BWX5 | NM_080473 | |
| 30824 | CXCL5: (SCYB5 OR ENA78) SMALL INDUCIBLE CYTOKINE B5 PRECURSOR (ENA-78). | P42830 Q96QE1 | NM_002994 | |
| 30827 | IFNE1: (IFNE1) INTERFERON EPSILON-1 (INTERFERON-EPSILON) (IFNT1)(UNQ360). | Q86WN2 | NM_176891 | |
| 30830 | IL17BR: (IL17RB OR IL17BR OR EVI27) INTERLEUKIN-17B RECEPTOR PRECURSOR (IL-17B RECEPTOR). | Q9NRM6 Q9BPZ0 Q9NRL4 Q9NRM5 | NM_018725 NM_172234 | |
| 30839 | IL9R: ((IL9RX OR IL9R) AND (IL9RY OR IL9R)) (IL-9R) (GFI-2) (CD129 ANTIGEN). | Q01113 Q14634 Q8WWU1 Q96TF0 | NM_002186 NM_176786 | 1.54/83% |
| 30842 | MAF_2: (MAF) TRANSCRIPTION FACTOR MAP (PROTO-ONCOGENE C-MAF). | O75444 Q9UP93 | NM_001031804 NM_005360 | |
| 30845 | MAF_3: (MAF) TRANSCRIPTION FACTOR MAF (PROTO-ONCOGENE C-MAF). | O75444 Q9UP93 | NM_001031804 NM_005360 | 1.15/20% |

The example set forth above is provided to give those of ordinary skill in the art a complete disclosure and description of how to make and use the embodiments of the apparatus, systems and methods of the disclosure, and is not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

A number of embodiments have been described. Nevertheless, it will be understood that various modifications may be made without departing from the spirit and scope of the description. Accordingly, other embodiments are within the scope of the following claims.

What is claimed is:

1. A method of monitoring a subject's responsiveness to an administered therapeutic agent, comprising:
   obtaining substantially purified neutrophils by filtration from a first biological sample from the subject at a first time point by either a noninvasive or minimally invasive method, wherein the filtration allows for the separation of cellular debris and epithelial cells from the neutrophils;
   quantifying the amounts of a set of biological factors in the neutrophils from the first biological sample, wherein the set of biological factors is quantified from cDNA made by reverse transcribing mRNA from the neutrophils;
   administering a therapeutic agent to the subject;
   obtaining substantially purified neutrophils by filtration from a second biological sample from the subject at a second time point by either a noninvasive or minimally invasive method, wherein the filtration allows for the separation of cellular debris and epithelial cells from the neutrophils;
   quantifying the amounts of a set of biological factors in the neutrophils from the second biological sample, wherein the set of biological factors is quantified from cDNA made by reverse transcribing mRNA from the neutrophils; and
   determining a change in the quantified biological factors between the neutrophils from the first sample and the neutrophils from the second sample, wherein the change in the biological factors between the first sample and the second sample is indicative of the subject's responsiveness to the administered therapeutic agent.

2. The method of claim 1, wherein the non-invasive method is selected from the group consisting of the collection of saliva, the collection of urine and the collection of fecal matter.

3. The method of claim 1, wherein the minimally invasive method is selected from the group consisting of swabbing the buccal or rectal region of a subject.

4. The method of claim 1, wherein the quantifying and determining steps are carried out using a computer comprising a computer program that instructs the computer to:
   quantify the amounts of a set of biological factors from substantially purified neutrophils from a first biological sample that has been obtained by a noninvasive or minimally invasive method, wherein the neutrophils are substantially purified by filtering the first biological sample to remove cellular debris and epithelial cells from the neutrophils, and wherein the set of biological factors is quantified from cDNA made by reverse transcribing mRNA from the neutrophils;
   store the quantified amounts from the first biological sample in a computer; quantify the amounts of a set of biological factors in factors from substantially purified neutrophils from a second biological sample that has been obtained by a noninvasive or minimally invasive method, wherein the neutrophils are substantially purified by filtering the second biological sample to remove cellular debris and epithelial cells from the neutrophils, and wherein the set of biological factors is quantified from cDNA made by reverse transcribing mRNA from the neutrophils; and
   determine a change in the quantified polynucleotides between the first sample and the second sample using the first stored quantified amounts and the second quantified amount, wherein the change in biological factors between the first sample and the second sample is indicative of the subject's responsiveness to the administered therapeutic agent;
   output the measured change in the subject's response to the administered therapeutic agent to a technician or user.

5. The method of claim 4, wherein the computer is at a remote location.

6. The method of claim 1, wherein the neutrophil is fixed in a fixative is added to the first and second biological samples prior to the filtration of the samples.

7. The method of claim 6, wherein the fixative is formaldehyde.

8. The method of claim 7, wherein the first and second biological samples comprise a concentration of 2.3% formaldehyde, and wherein the samples are stored at 4° C. prior to filtration.

9. The method of claim 1, wherein the mRNA encodes a cytokine.

10. The method of claim 1, wherein the biological factor is associated with a systemic biological reaction.

11. The method of claim 1, wherein the subject has a disease or disorder that can be treated by administering the therapeutic agent.

12. The method of claim 11, wherein the mRNA encodes biological factors associated with the disease or disorder.

13. A method of monitoring a subject's responsiveness to an administered therapeutic agent, comprising:
    obtaining a first salivary sample from the subject at a first time point by either a noninvasive or minimally invasive method;
    fixing a set of biological factors in the first salivary sample;
    administering a therapeutic agent to the subject;
    obtaining a second salivary sample from the subject at a second time point by either a noninvasive or minimally invasive method;
    fixing a set of biological factors in the second salivary sample;
    substantially purifying neutrophils from the first salivary sample and the second salivary sample by filtration, wherein the filtration allows for the separation of cellular debris and epithelial cells from the neutrophils;
    quantifying the biological factors in the first and the second salivary samples, wherein the set of biological factors is quantified from cDNA made by reverse transcribing mRNA from the neutrophils; and
    determining a change in the quantified biological factors between the first sample and the second sample,
    wherein the change in biological factors between the first sample and the second sample is indicative of the subject's responsiveness to the administered therapeutic agent.

14. The method of claim 13, wherein the fixing is accomplished by contacting the biological factors with a fixative agent.

15. The method of claim 14, wherein the fixative agent is formaldehyde or paraformaldehyde, picric acid, mercuric ions, glutaraldehyde, or alcohol.

16. The method of claim 15, wherein the fixative agent is formaldehyde.

17. The method of claim 15, wherein the fixative agent is alcohol.

* * * * *